United States Patent
Podila et al.

(10) Patent No.: US 7,057,087 B2
(45) Date of Patent: Jun. 6, 2006

(54) APPLICATION OF ASPEN MADS-BOX GENES TO ALTER REPRODUCTION AND DEVELOPMENT IN TREES

(75) Inventors: Gopi Krishna Podila, Houghton, MI (US); Leland James Cseke, Madison, AL (US); Banalata Sen, Durham, NC (US); David F. Karnosky, Chassell, MI (US)

(73) Assignee: Board of Control of Michigan Technological University, Houghton, WI (US)

( * ) Notice: Subject to any disclaimer, the term of this patent is extended or adjusted under 35 U.S.C. 154(b) by 299 days.

(21) Appl. No.: 10/206,653

(22) Filed: Jul. 26, 2002

(65) Prior Publication Data

US 2004/0019933 A1    Jan. 29, 2004

(51) Int. Cl.
*C12N 15/29* (2006.01)
*C12N 15/82* (2006.01)
*C12N 15/87* (2006.01)
*C12N 5/04* (2006.01)
*A01H 5/00* (2006.01)

(52) U.S. Cl. .................. 800/278; 800/290; 800/298; 800/317.3; 800/287; 800/300; 536/23.1; 536/23.6; 435/320.1; 435/410; 435/419; 435/468

(58) Field of Classification Search ............... 536/23.1, 536/23.6, 24.1; 800/278, 290, 298, 300, 800/317.3, 287; 435/69.1, 468, 320.1, 410, 435/419

See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,987,071 A | 1/1991 | Cech et al. | |
| 5,231,020 A | 7/1993 | Jorgensen et al. | |
| 5,231,021 A | 7/1993 | Chatterjee | |
| 5,432,068 A | 7/1995 | Albertsen et al. | |
| 5,443,974 A | 8/1995 | Hitz et al. | |
| 5,451,514 A | 9/1995 | Boudet et al. | |
| 5,455,167 A | 10/1995 | Voelker et al. | |
| 5,530,192 A | 6/1996 | Murase et al. | |
| 5,543,508 A | 8/1996 | Haseloff et al. | |
| 5,583,021 A | 12/1996 | Dougherty et al. | |
| 5,659,124 A | 8/1997 | Crossland et al. | |
| 5,686,649 A | 11/1997 | Chua et al. | |
| 5,861,542 A * | 1/1999 | An | 800/278 |

FOREIGN PATENT DOCUMENTS

| EP | 0 709 462 A2 | 5/1996 |
|---|---|---|
| WO | WO 00/23578 | 4/2000 |

OTHER PUBLICATIONS

Kano-Murakami et al (1993, FEBS 334:365-368).*

Bowie et al, Science 247:1306-1310, 1990.*
McConnell et al, Nature 411 (6838):709-713, 2001.*
Fourgoux-Nicol et al (1999, Plant Molecular Biology 40:857-872).*
Sung et al (1997; Plant Cell Physiol. 38(4):484-489).*
Han et al, Biology of Populus and its Implications for Management and Conservation, Part 1, Chapter 9, pp. 201-222, NRC Research Press, Nat. Res. Coun. of Canada, Ottawa, Ontario (1996).*
Ausubel et al., *Current Protocols in Molecular Biology*, Current Protocols and John Wiley & Sons, Inc. (1987-2003). (Cover page, copyright page and table of contents only).
Karnosky, D.F., B. Sen, J. Kim, B. Xiang, X. Lu, L. Cseke, D. Dixon, J.J. Liu, G. Wyckoff, and Gopi K. Podila, "Engineering reproductive sterility in forest trees," *Proc. International Workshop BIO-REFOR*. Nepal, 1999, pp. 7-11 (2000).
Kim, "Genetic Engineering of Populus Species to Improve Resistance to Environmental Stresses", *Ph. D. Thesis. Michigan Technological University*, 111 pp. (1998).
Kooter et al., *Mol, Current Opin. Biol.* 4:166-171 (1993)(cover page, copyright page only).
Pei-Show Juo, *Concise Dictionary of Biomedicine and Molecular Biology* CRC Press 2d ed. (2002).
Sanger et al., *Plant Mol. Biol.* 14:433 (1990).
Stettler, *Popular Molecular Network Newsletter* 1(1), College of Forest Resources AR-10, University of Washington, Seattle, Wash. (1993).

(Continued)

*Primary Examiner*—David T. Fox
*Assistant Examiner*—Stuart F. Baum
(74) *Attorney, Agent, or Firm*—Michael Best & Friedrich, LLP

(57) ABSTRACT

The present invention provides compositions and methods for producing a transgenic plant that exhibits altered characteristics resulting from over expression or under expression of a novel polypeptide PtM3 or its homolog PtM4. The altered characteristics resulting from over-expression include at least one of the ability to convert axillary meristem to floral meristem; to accelerate flowering i.e., early flowering; to increase fruit production; to increase nut production; to increase seed output; to increase branching; to increase flower production; to increase fruit yield; to increase flower yield and a combination thereof. The altered characteristics resulting from suppressed expression include at least one of complete sterility; partial sterility (sterility of only one sex of a bisexual plant); reduced pollen production; decreased flowering; increased biomass and combinations thereof. Furthermore, once the transgenic plant is sterile, additional exogenous sequences may be incorporated into the sterile plant genome, resulting in other desired plant characteristics. Related promoter, gene constructs, methods, antibodies and kits are also provided.

30 Claims, 8 Drawing Sheets

OTHER PUBLICATIONS

Strauss et al., *TGERC Annual Report*: 1994-1995 Forest Research Laboratory, Oregon State University (1995b).
An, *Plant Molecular Biology*, 25:335-337, 1994.
Klopfenstein et al., "Micropropagation, Genetic Engineering and Molecular Biology of Populus" *USDA Forest Service Gen Tech. Rep. RM-GTR-297*,326 (1997). (Cover page, copyright page and table of contents only.).
Ainley et al., Regulatable endogenous production of cytokinins up to "toxic" levels in transgenic plants and plant tissues, *Plant Mol. Biol.* 22:13-23 (1993).
Altschul, S. F. et al., *J. Mol. Biol.* 215:403-410 (1990).
An, *Plant Physiol.* 81:86 (1986).
Angenent et al., *Plant Cell* 4:983-993 (1992).
Angenent et al., *The Plant Journal* 4:101-112 (1993).
Ausubel et al., *Current Protocols in Molecular Biology*, Greene Publishing and Wiley-Interscience: New York (1987).
Ausubel et al., *Current Protocols in Molecular Biology*, John Wiley Press, NY (2001).
Beaucage and Carruthers, *Tetra. Letts.* 22:1859-1862 (1981).
Benfey and Chua, *Science* 250:959-966 (1990).
Boerjan et al., "Genetic Modification of Lignin Biosynthesis In Quaking Aspen And Poplar",*USDA Forest Service Gen. Tech. Rep. RM-GTR-297*, 193-205 (1997).
Boerjan W, Baucher M, Chabbert B, Petit-Conil M, Leple JC, Pilate G, Cornu D, Monties B, Inze D, Van Doorsselaere J, Jouanin L and Van Monatgu M, with Tsai C-J, Podila GK and Chiang VL, Genetic modification of lignin biosynthesis in quaking aspen and poplar. *In: Klopfenstein NB*, Chun YW, Kim MS, Ahuja MR, eds Dillon, MC, Carman RC, Eskew LG, tech eds. Micropropagation, genetic engineering and molecular biology of Populus. *Gen. Tech. Rep* RM-GTR-297. Fort Collins, CO: USDA, Forest Service, Rocky Mountain research station. pp. 193-205 (1997) Same as Reference "AY".
Bourque and Folk, *Plant Mol. Biol.* 19:641-647 (1992).
Bradley et al., *Cell* 72:85-95 (1993).
Cannon et al., *Plant Mol. Biol.* 15:39-47 (1990).
Chang et al., "*Saccharomyces cerevisiae* secretes and correctly processes human interferon hybrid protein containing yeast invertase signal peptides," *Mol. and Cell. Biol.* 6:1812-1819 (1986).
Coen, *Annu. Rev. Plant Physiol. Plant Mol. Biol.* 42:241-279 (1991).
Davies et al., "Alteration of tobacco floral organ identity by expression of combinations of *Antirrhinum* MADS-box genes", *The Plant Journal* 10(4): 663-677 (1996).
Denis et al., Expression of engineered nuclear male sterility in *Brassica napus. Plant Physiol.* 101: 1295-1304 (1993).
Duan et al., *Nature Biotech.* 14:494-498 (1996).
Ellis et al., *Bio/Technology* 11:84-89 (1993).
Engvall, *Enzymol.* 70:419 (1980).
Fan et al., "Specific interactions between the K domains of AG and AGLs, members of the MADS domain family of DNA binding proteins", *The Plant Journal* 12(5): 999-1010 (1997).
Fisher, *Manual of Clinical Immunology*, Ch. 42 (1980).
Flavell, *Proc. Natl. Acad. Sci. USA* 91:3490-3496 (1994).
Gan and Amasino, Inhibition of leaf senescence by autoregulated production of cytokinin. *Science* 270:1986-1988 (1995).
Gatz, Chemical control of gene expression. *Ann. Rev. Plant Physiol. Plant Mol. Biol.* 48:89-108 (1997).

Glick and Thompson (eds.), Methods in Plant Molecular Biology and Biotechnology, Boca Raton, Fla.: CRC Press (1993).
Guide to Protein Purification, ed. Deutscher, Meth. Enzymol. 185, Academic Press, San Diego (1990).
Han et al., Cellular and molecular biology of Agrobacterium-mediated transformation of plants and its application to genetic transfonnation of Populus. In: Stettler et al., [eds.] Biology of Populus and its Implications for Management and Conservation, Part I, Chapter 9, pp. 201-222, NRC Research Press, Nat. Res. Coun. of Canada, Ottawa, Ontario (1996).
Harlow and Lane, *Antibodies, A Laboratory Manual*, Cold Spring Harbor Laboratory, New York (1988).
Hemerly et al., *Plant Cell* 5:1711-1723 (1993).
Higgins, D.G., Thompson, J.D. and Gibson, T.J., Using CLUSTAL for multiple sequence alignments. *Methods Enzymol.* 266, 383-402 (1996).
Honma et al., "Complexes of MADS-box proteins are sufficient to convert leaves into floral organs", *Nature* 409: 525-529 (2001).
Huang et al., *The Plant Cell* 8:81-94 (1996).
Huijser et al., *EMBO J.* 11:1239-1249 (1992).
Huse et al., *Science* 246:1275-1281 (1989).
Innis et al., *PCR Protocols: A Guide to Methods and Applications*, Academic Press, San Diego (1990).
Jack et al., *Cell* 68:683-697 (1992).
Jeanmougin, F., Thompson, J.D., Gouy, M., Higgins, D.G. and Gibson, T.J., "Multiple sequence alignment with Clustal X. Trends," *Biochem Sci*, 23, 403-5 (1998).
Jefferson et al., *EMBO J.* 6:3901-3907 (1987).
Kandasamy et al., "Ablation of papillar cell function in Brassica flowers results in the loss of stigma receptivity to pollination," *Plant Cell* 5:263-275 (1993).
Kanehisa, *Nuc. Acids Res.* 12:203-213 (1984).
Kempin et al., *Plant Physiol.* 103:1041-1046 (1993).
Klein et al., *Nature* 327:70-73 (1987).
Köhler and Milstein, *Nature* 256:495 (1975).
Kooter et al., *Mol. Current Opin. Biol.* 4:166-171 (1993).
Kooter et al., *Trends Plant Sci.*, 4, 340-346 (1999).
Kuhlemeier et al., *Plant Cell* 1:471 (1989).
Lengauer et al., *Hum. Mol. Genet.* 2:505-512 (1993).
Liang and Richardson, "Expression and characterization of human lactoferrin in yeast (*Saccharomyces cerevisiae*)," *J. Agric. Food Chem.* 41:1800-1807 (1993).
Ma et al., *Genes Devel.* 5:484-495 (1991).
Mandel and Yanofsky, *Plant Cell* 7:1763-1771 (1995).
Mandel et al., *Cell* 71:133-143 (1992).
Mandel et al., *Nature* 360:273-277 (1992).
Marcotte et al., *Plant Cell* 1:969 (1989).
Mariani et al., A chimeric ribonuclease-inhibitor gene restores fertility to male-sterile plants. *Nature* 357:384-387 (1992).
Matteucci et al., *J. Am. Chem. Soc.* 103:3185 (1981).
McCown et al., "Stable transformation of Populus and incorporation of pest resistance by electric discharge particle acceleration," *Plant Cell Rep.* 9:590-594 (1991).
Merrifield, *J. Amer. Chem. Soc.* 85:2149-2156 (1963).
Mizukami et al., *Plant Cell* 8:831-845 (1996).
Needleman and Wunsch, *J. Mol. Biol.* 48: 443-453, (1970).
Norman et al., *Cell* 55:989-1003 (1988).
Odell et al., "Seed specific gene activation mediated by the Cre/lox site-specific recombination system," *Plant Physiol.* 106:447-458 (1994).
Odell et al., *Nature* 313:810-812 (1985).

Ouchterlony et al., In Handbook of Experimental Immunology, Wier, D. (ed.) chapter 19. Blackwell (1973).
Pappenheimer, "Diphtheria toxin," Annu. Rev. Biochem. 46:69-94 (1977).
Passmore et al., J. Mol. Biol. 204:593-606 (1988).
Pearson W. R. et al., Proc. Natl. Acad. Sci., 85:2444-2448 (1988).
Pelaz et al., "B and C floral organ identity functions require SEPALLATA MADS-box gene", Nature, 405:200-203 (2000).
Pinkel et al., Proc. Natl. Acad. Sci. USA 85:9138-9142 (1988).
Pnueli et al., The Plant Cell, vol. 6, 175-186 (1994).
Pouwels et al., Cloning Vectors: A Laboratory Manual, 1985 supplement (1987).
Purugganan et al., Genetics 140:345-356 (1995).
Riechmann et al. Biol. Chem. 378:1079-1101 (1998).
Sambrook et al., at 9.47-9.52, 9.56-9.58 (1989).
Sambrook et al., Molecular Cloning: A Laboratory Manual, 2$^{nd}$ ed., vol. 1-3, ed. Cold Spring Harbor Laboratory Press: Cold Spring Harbor, N.Y. (1989).
Sanger et al. Proc. Natl. Acad. Sci. 74: 5463-5467 (1977).
Savidge et al. "Temporal Relationship Between the Transcription of Two Arabidopsis MADS Box Genes and the Floral Organ Identity Genes", The Plant Cell, 7:721-733 (1995).
Schäffner and Sheen, Plant Cell 3:997 (1991).
Schmidt et al., Plant Cell 5:729-737 (1993).
Schmülling et al., "Restoration of fertility by antisense RNA in genetically engineered male sterile tobacco plants," Mol. Gen. Genet.237-385-394 (1993).
Scopes, "Protein Purification: Principles and Practice," Springer Verlag, New York (1982).
Sheppard et al., "A DEFICIENS Homolog from the Dioecious Tree Black Cottonwood is Expressed in Female And Male Floral Meristems of the Two-Whorled, Unisexual Flowers," Plant Physiology, 124:627-639 (2000).
Shimamoto, Curr. Opin. Biotech. 5:158-162 (1994).
Siebertz et al., Plant Cell 1:961 (1989).
Singer et al., Plant Mol. Biol. 14:433 (1990)
Sommer et al., EMBO J. 11:251-263 (1990).
Southerton et al., "Eucalyptus has a functional equivalent of the Arabidopsis floral meristem identity gene LEAFY," Plant Mol. Biol., 37:897-910 (1998).
Strauss et al., Molecular Breeding 1:5-26 (1995a).

Tandre et al., "Conservation of gene structure and activity in the regulation of reproductive organ development of conifers and angiosperms", The Plant Journal, 15(5):615-623 (1998).
Tang et al., Nature (London) 356:152-154 (1992).
Thompson, J.D., Gibson, T.J., Plewniak, F., Jeanmougin, F. and Higgins, D.G., "The Clustal X windows interface: flexible strategies for multiple sequence alignment aided by quality analysis tools," Nucleic Acids Research, 24:4876-4882 (1997).
Tröbner et al., EMBO J. 11:4693-4704 (1992).
Tsai CJ, Popko JL, Mielke MR, Hu WJ, Podila GK, Chiang VL., "Suppression of O-methytransferase gene by homologous sense transgene in quaking aspen causes red-brown wood phenotypes," Plant Physiol. 117: 101-12 (1998).
Tsai et al., "Agrobacterium-mediated transformation of quaking aspen (Populus tremuloides) and regeneration of transgenic plants," Plant Cell Reports, 14: 94-97 (1994).
Tsai et al., "Suppression of O-Methyltransferase Gene by Homologous Sense Transgene in Quaking Aspen Causes Red-Brown Wood Phenotypes", Plant Physiol 117:101-112 (1998).
Tsai, C. J., Podila, G. K. and Chiang, V. L., "Agrobacterium-mediated transformation of quaking aspen (Populus tremuloides) and regeneration of transgenic plants," Plant Mol. Biol. 14: 94-97 (1994). Same as Reference "EL".
Vaitukaitis et al., J. Clin. Endocrinol. Metab. 33:988-991 (1971).
Van der Meer et al., The Plant Cell vol. 4:253-262 (1992).
Wang et al., (eds), "Transformation of Plants and Soil Microorganisms," Cambridge, UK: University Press (1995).
Weigel et al., "The ABCs of Floral Homeotic Genes," Cell, 78:203-209 (1994).
Weigel, Ann. Rev. Genetics 29:19-39 (1995).
Weissbach and Weissbach, "Methods for Plant Molecular Biology," Academic Press (1989).
Wetmur and Davidson, J. Mol. Biol. 31:349-370, (1968).
Worrall et al., "Premature dissolution of the microporocyte callose wall causes male sterility in transgenic tobacco," Plant Cell 4:759-771 (1992).
Yanofsky et al., Nature 346:35-39 (1990).
Yanofsky, Ann. Rev. Plant Physiol. Plant Mol. Biol. 46:167-188 (1995).

* cited by examiner

FIG. 1

PtM3 cDNA sequence and corresponding amino acid sequence

```
  1 AGAAGACAACCGAAGCACTTCTTTAAACTTATAACTTTCTCTTTCTACAAACATTTGTTG    60
 61 TTCTCTCTATTATTGTTAAGGAATATGGGGAGAGGTAGAGTGGAGCTGAAGAGGATAGAG   120
                          M  G  R  G  R  V  E  L  K  R  I  E

121 AACAAGATAAACAGGCAGGTGACATTTGCAAAGAGGAGAAATGGGTTGTTGAAGAAAGCT   180
     N  K  I  N  R  Q  V  T  F  A  K  R  R  N  G  L  L  K  K  A

181 TATGAGTTATCTGTGCTCTGTGATGCTGAGGTTGCTCTCATCATCTTCTCTAACCGTGGC   240
     Y  E  L  S  V  L  C  D  A  E  V  A  L  I  I  F  S  N  R  G

241 AAGCTCTACGAGTTTTGTAGCACATCTAACATGCTGAAGACCCTGGAAAGGTATCAGAAG   300
     K  L  Y  E  F  C  S  T  S  N  M  L  K  T  L  E  R  Y  Q  K

301 TGCAGCTATGGTGCAGAAGAAGTCAATAAACCAGCCAAGGAGCTCGAGAACAGCTACAGG   360
     C  S  Y  G  A  E  E  V  N  K  P  A  K  E  L  E  N  S  Y  R

361 GAGTACTTGAAAGTGAAAGCAAGATTTGAGGGCCTACAACGAACTCAGAGGAACCTTCTT   420
     E  Y  L  K  V  K  A  R  F  E  G  L  Q  R  T  Q  R  N  L  L

421 GGAGAGGACCTCGGACCTCTGAATACCAAAGACCTTGAGCAGCTCGAGCGTCAGTTAGAG   480
     G  E  D  L  G  P  L  N  T  K  D  L  E  Q  L  E  R  Q  L  E

481 TCGTCATTGAACCAAGTTCGGTCAACTAAGACCCAGTATATGCTCGACCAACTTGCTGAT   540
     S  S  L  N  Q  V  R  S  T  K  T  Q  Y  M  L  D  Q  L  A  D

541 CTTCAAAATAAGGAACATCTGTTGCAGGAAGCTAACAGAGGTTTGACAATAAAGCTGGAT   600
     L  Q  N  K  E  H  L  L  Q  E  A  N  R  G  L  T  I  K  L  D

601 GAAATCAGTGCAAGAAATAGCCTCCGACCATCATGGGAAGGTGATGATCAGCAAAATATG   660
     E  I  S  A  R  N  S  L  R  P  S  W  E  G  D  D  Q  Q  N  M

661 TCCTACGGCCACCAGCATGCTCAGTCTCAGGGGCTATTCCAGGCTTTGGAATGCAATCCC   720
     S  Y  G  H  Q  H  A  Q  S  Q  G  L  F  Q  A  L  E  C  N  P

721 ACTTTGCAAATAGGCTACAACCCTGTTGGTTCAGACCAGGTGTCTGCAATAACACATGCC   780
     T  L  Q  I  G  Y  N  P  V  G  S  D  Q  V  S  A  I  T  H  A

781 ACCCAGCAAGTCCATGGGTTCATTCCAGGATGGATGCTTTGAGTTTTGTGCTCTTCATTG   840
     T  Q  Q  V  H  G  F  I  P  G  W  M  L  *

841 CTCATAAAGGAGCACCTACCATGTAACTTTCTCTCTTGGTGTTGGTAATGTGTAAATGAT   900
901 TTCAAGAGCATGTGTACTTTCATTTGGACA                                 930
```

FIG. 2

PtM4 cDNA sequence and corresponding amino acid sequence

```
  1 GTGTGGTATATGGGGAGAGGTAGAGTGGAGCTGAAGAGGATAGAAAACAAAATTAATCGG  60
                M   G   R   G   R   V   E   L   K   R   I   E   N   K   I   N   R

61 CAGGTGACATTTGCAAAGAGGAGAAATGGGTTGTTGAAGAAAGCTTATGAGTTATCTGTG 120
      Q   V   T   F   A   K   R   R   N   G   L   L   K   K   A   Y   E   L   S   V

121 CTCTGTGATGCTGAGGTTGCTCTCATCATCTTCTCTAACCGTGGCAAGCTCTACGAGTTT 180
      L   C   D   A   E   V   A   L   I   I   F   S   N   R   G   K   L   Y   E   F

181 TGTAGCACATCTAACATGCTGAAGACCCTGGAAAGGTATCAGAAGTGCAGCTATGGTGCA 240
      C   S   T   S   N   M   L   K   T   L   E   R   Y   Q   K   C   S   Y   G   A

241 GAAGAAGTCAATAAACCAGCCAAGGAGCTCGAGAACAGCTACAGGGAGTACTTGAAAGTG 300
      E   E   V   N   K   P   A   K   E   L   E   N   S   Y   R   E   Y   L   K   V

301 AAAGCAAGATTTGAGGCCCTACAACGAACTCAGAGGAACCTTCTTGGAGAGGACCTCGGA 360
      K   A   R   F   E   A   L   Q   R   T   Q   R   N   L   L   G   E   D   L   G

361 CCTCTGAATACCAAAGATCTTGAGCAGCTCGAGCGTCAGTTAGAGTCGTCATTGAACCAA 420
      P   L   N   T   K   D   L   E   Q   L   E   R   Q   L   E   S   S   L   N   Q

421 GTTCGGTCAACTAAGACCCAGTATATGCTCGACCAACTTGCTGATCTTCAAAATAAGGAA 480
      V   R   S   T   K   T   Q   Y   M   L   D   Q   L   A   D   L   Q   N   K   E

481 CATCTGTTGCTGGAAGCTAACAGAGGTTTGACAATAAAGCTGGATGAAATCAGTGCAAGA 540
      H   L   L   L   E   A   N   R   G   L   T   I   K   L   D   E   I   S   A   R

541 AATAGCCTCCGACCATCATGGGAAGGTGATGATCAGCAAAATATGTCCTACGGNCACCAG 600
      N   S   L   R   P   S   W   E   G   D   D   Q   Q   N   M   S   Y   G   H   Q

601 CACGCTCAGTCTCAGGGGCTATTCCAGGCTTTGGAATGCAATCCCACTTTGCAAATAGGC 660
      H   A   Q   S   Q   G   L   F   Q   A   L   E   C   N   P   T   L   Q   I   G

661 TACAACGCTGTTGGTTCAGACCAGGTGTCTGCAATAACACATGCCACCCAGCAAGTCCAT 720
      Y   N   A   V   G   S   D   Q   V   S   A   I   T   H   A   T   Q   Q   V   H

721 GGGTTCATTCCAGGATGGATGCTTTGAGTTTTGTGTTCTTCATTGCTCATAAAGGAGCAC 780
      G   F   I   P   G   W   M   L   *
781 CTACCATGTAACTTTCTCTCTTGGTGTTGGTAATGTGTAAATGATTTCAAGAGCATGTGT 840
841 ACTTTCATTTGGACATGAAAACTTTATGTGGCTGGATTTCAGAACTTTAGCCAGGGACAC 900
901 GAGGCATGTAAAAG                                               914
```

FIG. 3

ClustalW Alignment of predicted amino acid sequences of *PtM3* and *PtM4*

```
PTM3   1   MGRGRVELKRIENKINRQVTFAKRRNGLLKKAYELSVECDAEVALIIFSNRGKLYEFCSTSNMLKTLERYQKCSYGAEEVNKPAKELENS
PTM4   1   MGRGRVELKRIENKINRQVTFAKRRNGLLKKAYELSVLCDAEVALIIFSNRGKLYEFCSTSNMLKTLERYQKCSYGAEEVNKPSKELENS
PTM3  91   YREYLKVKARFEALQRTQRNLLGEDLGPLNTKDLEQLERQ-LESSLNQVRSTKTQYMLDQLADLQNKEHLLLEANRGLTIKLDEISARNS
PTM4  91   YREYLKVKARFEALQRTQRNLLGEDLGPLNTKIL-QLERQLLESSLNQVRSTKPQYMLDQLADLQKKEHLLLEANRGLTIKLDEISARNS
PTM3 180   LRPSWEGDDQQNMSYGHQHAQSQGLFQALECNPTLQIGYNFVGSDQVSAITHATQQVHGFIPGWML
PTM4 180   LRPSWEGDDQQNMSYGHQHAQSQGLFQALECNPTLQIGYNAVGSDQVSAITHATQQVHGFIPGWML
```

Phylogenetic tree of predicted amino acid sequences of *PtM3* (male dominant expression) and *PtM4* (female dominant expression) compared to various floral and tree MADS-box sequences

FIG. 5

PtM3 5' untranslated region (UTR) containing PtM3 promoter and intron sequence

```
   2 GGCCCGGCTGGTTCTCATGTTGGACTCCGACTTTAATTACTTTAACTACAAGCTTATTAT   61
  62 AATTTTTTTTTATACTATTTTATTTCATTTCAGTATTTAAACATTATTGTTTATATAAA  121
 122 AAAATAGTTGAGCCCGTGGCAAAGCATAAACCAAGACCGAATATTCTAAATACTAAATTT  181
 182 CTAGTTTGTTTGATTTCTCAATGCCCCGAACAGTAACGCTGTAATCAGACAACCTCATCC  241
 242 GGACAAGCCAAATCAAGAACTTTCTCCAGTATCAAACCGACACGTGGAGGAGCTCCATTT  301
 302 TAAGGGAGGGGACTACTTTCTGCCACGTGTGGAAACATCTGGAAATGACAAATTGATGCC  361
 362 ATATAAAATTTTCTTACATGAAAGGACCACTGTCCCTTTTACGCCCCACCGCAGCGCGT  421
 422 GACCACACTTACAACCCTACCTCCAACAACACTGACACAATGACCGAGACGGTGGCGCGT  481
 482 GAATACACTCTCCAAACTTAGAACCTACGTTCGTAATCAATGATGTGACAAAAAAGTAAA  541
 542 AACCAAGAAGCTTTGAAAGCTAATAAATGAATTACTATATATATTATATCAATTCTTCAA  601
 602 GAAAATTGGAAGAAATTATTTTTTTTCAATTTAATTTATAAATATAACTATTTAATGGGG  661
 662 AAAGACTTCTATCCTTTGGAACCTTAATTGGAAAAGCAGCAACCCCATGCCGTTAACTTG  721
 722 AAAAAAAACGAAACCCGGGTGTATTAAAAACTTACCAACAAGGGGGTAACCTTCCACTAA  781
 782 CCGTGTACAATGGCAAAGTAACCCAACTTAAGGAAAAAGATTCCATAAATAAAACCATTT  841
 842 TCAAAATGTAAAATATTTTTTCAAATATTTATAAATAACTATATTAATGTGAAAGCCATC  901
 902 ATAATCCCGATTAGGAGATACTTAATTAGGAGAAAGTCAAGTCGAGAACCCCATTGCCG  961
 962 TTAATACTTGAAAAATAAACCAGTAAAATACACAGAGGTTGCATGTAACTAGAAAGAACA 1021
1022 GCTAACCCTAAGCTGCATTTCTTTTCTATATATATATATATATATAACAGAAAAGAAGAA 1081
1082 GACAACCGAAGCACTTCTTTAAACTTATAACTTTCTCTTTCTACAAACATTTGTTGTTCT 1141
              5'UTR Intron →
1142 CTCTATTATTGGTGGGTCTTTCTTTCTCTAGGGTTTCTTTAAAATATCTAACTTTCTC   1201

1202 TTCGTTTTTCACTTATTTGTTACAGTTTGGGTTCTGATTCCTAAAAGTGTAGATCACCT   1261

1262 TCTTCTTGCTCTTGAGAGAAGAACAAGAAACGAAAAAAAAAACAAAAGAAAAGGAAAGAT   1321

1322 ATAAAGGAAATAAAGACTAATACAAAAGTAAATATATCATTAACTTACATGGTTAGATTT   1381
                                              ← 5'UTR Intron
1382 ATGTATTAATTATAACGAAAGATGGTTTTTTATTTGGTTTTTTTTGGCTTGTGATTATAG   1441

1442 TTAAGGAATATGGGGAGAGGTAGAGTGGAGCTGAACA                         1478
              M  G  R  G  R  V  E  L  K
              ▲
         Start codon for PtM3
```

Flower specific mRNA expression of *PtM3*

Transgenic plants over-expressing *PtM3*

Transgenic plants containing antisense PtM3

SEQUENCE LISTING

<160> NUMBER OF SEQ ID NOS: 11

<210> SEQ ID NO 1
<211> LENGTH: 930
<212> TYPE: DNA
<213> ORGANISM: Aspen

<400> SEQUENCE: 1
agaagacaac cgaagcactt ctttaaactt ataactttct ctttctacaa acatttgttg    60

```
ttctctctat tattgttaag gaatatgggg agaggtagag tggagctgaa gaggatagag      120
aacaagataa acaggcaggt gacatttgca agaggagaa atgggttgtt gaagaaagct       180
tatgagttat ctgtgctctg tgatgctgag gttgctctca tcatcttctc taaccgtggc      240
aagctctacg agttttgtag cacatctaac atgctgaaga ccctggaaag gtatcagaag      300
tgcagctatg gtgcagaaga agtcaataaa ccagccaagg agctcgagaa cagctacagg      360
gagtacttga aagtgaaagc aagatttgag ggcctacaac gaactcagag gaaccttctt      420
ggagaggacc tcggacctct gaataccaaa gaccttgagc agctcgagcg tcagttagag      480
tcgtcattga accaagttcg gtcaactaag acccagtata tgctcgacca acttgctgat      540
cttcaaaata ggaacatct gttgcaggaa gctaacagag gtttgacaat aaagctggat       600
gaaatcagtg caagaaatag cctccgacca tcatgggaag tgatgatca gcaaaatatg       660 tcctacggcc accagcatgc tcagtctcag gggctattcc aggctttgga atgcaatccc      720
actttgcaaa taggctacaa ccctgttggt tcagaccagg tgtctgcaat aacacatgcc      780
acccagcaag tccatgggtt cattccagga tggatgcttt gagttttgtg ctcttcattg      840
ctcataaagg agcacctacc atgtaacttt ctctcttggt gttggtaatg tgtaaatgat      900
ttcaagagca tgtgtacttt catttggaca                                      930

<210> SEQ ID NO 2
<211> LENGTH: 914
<212> TYPE: DNA
<213> ORGANISM: Aspen
<220> FEATURE:
<221> NAME/KEY: misc_feature
<223> OTHER INFORMATION: n = a or g or c or t/u

<400> SEQUENCE: 2
gtgtggtata tggggagagg tagagtggag ctgaagagga tagaaaacaa aattaatcgg       60
caggtgacat ttgcaaagag gagaaatggg ttgttgaaga agcttatga gttatctgtg       120 ctctgtgatg ctgaggttgc tctcatcatc ttctctaacc gtggcaagct ctacgagttt      180
tgtagcacat ctaacatgct gaagaccctg gaaaggtatc agaagtgcag ctatggtgca      240
gaagaagtca ataaccagc caaggagctc gagaacagct acagggagta cttgaaagtg      300
aaagcaagat tgaggcccct acaacgaact cagaggaacc ttcttggaga ggacctcgga     360
cctctgaata ccaaagatct tgagcagctc gagcgtcagt tagagtcgtc attgaaccaa     420
gttcggtcaa ctaagaccca gtatatgctc gaccaacttg ctgatcttca aaataaggaa      480
catctgttgc tggaagctaa cagaggtttg acaataaagc tggatgaaat cagtgcaaga     540
aatagcctcc gaccatcatg ggaaggtgat gatcagcaaa atatgtccta cggncaccag    600
cacgctcagt ctcaggggct attccaggct ttggaatgca atcccacttt gcaaataggc      660
tacaacgctg ttggttcaga ccaggtgtct gcaataacac atgccaccca gcaagtccat     720
gggttcattc caggatggat gctttgagtt ttgtgttctt cattgctcat aaaggagcac    780
ctaccatgta actttctctc ttggtgttgg taatgtgtaa atgatttcaa gagcatgtgt     840
actttcattt ggacatgaaa actttatgtg gctggatttc agaactttag ccagggacac     900
gaggcatgta aaag                                                       914

<210> SEQ ID NO 3
<211> LENGTH: 1477
<212> TYPE: DNA
<213> ORGANISM: Aspen
```

```
<400> SEQUENCE: 3
ggcccggctg gttctcatgt tggactccga ctttaattac tttaactaca agcttattat      60 aattttttt tttatactatt ttatttcatt tcagtattta acattattg tttatataaa     120 aaaatagttg agcccgtggc aaagcataaa ccaagaccga atattctaaa tactaaattt     180
ctagtttgtt tgatttctca atgccccgaa cagtaacgct gtaatcagac aacctcatcc     240
ggacaagcca aatcaagaac tttctccagt atcaaaccga cacgtggagg agctccattt     300
taagggaggg gactactttc tgccacgtgt ggaaacatct ggaatgaca aattgatgcc     360 atataaaatt ttcttacatg aaaggaccac tgtccctttt tacgcccac cgcagcgcgt     420 gaccacactt acaaccctac ctccaacaac actgacacaa tgaccgagac ggtggcgcgt     480
gaatacactc tccaaactta gaacctacgt tcgtaatcaa tgatgtgaca aaaaagtaaa     540
aaccaagaag ctttgaaagc taataaatga attactatat atattatatc aattcttcaa     600
gaaaattgga agaaattatt tttttcaat ttaatttata aatataacta tttaatgggg     660
aaagacttct atcctttgga accttaattg gaaaagcagc aaccccatgc cgttaacttg     720
aaaaaaaacg aaacccgggt gtattaaaaa cttaccaaca agggggtaac cttccactaa     780
ccgtgtacaa tggcaaagta acccaactta aggaaaaaga ttccataaat aaaaccattt     840
tcaaaatgta aaatattttt tcaaatattt ataaataact atattaatgt gaaagccatc     900
ataatcccga ttaggagata cttaattagg agaaagtcaa gtcgagaacc cccattgccg     960
ttaatacttg aaaaataaac cagtaaaata cacagaggtt gcatgtaact agaaagaaca    1020 gctaaccta agctgcattt cttttctata tatatatata tatataacag aaaagaagaa    1080
gacaaccgaa gcacttcttt aaacttataa cttctctttt ctacaaacat tgttgttct    1140 ctctattatt ggtgggtctt tctttctctc tagggtttct ttaaaatatc taactttctc    1200 ttcgttttc acttattttg ttacagtttg ggttctgatt cctaaaagtg tagatcacct    1260
tcttcttgct cttgagagaa gaacaagaaa cgaaaaaaaa aacaaaagaa aaggaaagat    1320
ataaaggaaa taaagactaa tacaaaagta aatatatcat taacttacat ggttagattt    1380
atgtattaat tataacgaaa gatggttttt tatttggttt tttttggctt gtgattatag    1440
ttaaggaata tggggagagg tagagtggag ctgaaga                              1477

<210> SEQ ID NO 4
<211> LENGTH: 245
<212> TYPE: PRT
<213> ORGANISM: Aspen

<400> SEQUENCE: 4

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Thr Ser Asn Met Leu
    50                  55                  60

Lys Thr Leu Glu Arg Tyr Gln Lys Cys Ser Tyr Gly Ala Glu Glu Val
65                  70                  75                  80

Asn Lys Pro Ala Lys Glu Leu Glu Asn Ser Tyr Arg Glu Tyr Leu Lys
                85                  90                  95
```

```
Val Lys Ala Arg Phe Glu Gly Leu Gln Arg Thr Gln Arg Asn Leu Leu
            100                 105                 110

Gly Glu Asp Leu Gly Pro Leu Asn Thr Lys Asp Leu Glu Gln Leu Glu
            115                 120                 125

Arg Gln Leu Glu Ser Ser Leu Asn Gln Val Arg Ser Thr Lys Thr Gln
130                 135                 140

Tyr Met Leu Asp Gln Leu Ala Asp Leu Gln Asn Lys Glu His Leu Leu
145                 150                 155                 160

Gln Glu Ala Asn Arg Gly Leu Thr Ile Lys Leu Asp Glu Ile Ser Ala
                165                 170                 175

Arg Asn Ser Leu Arg Pro Ser Trp Glu Gly Asp Asp Gln Gln Asn Met
            180                 185                 190

Ser Tyr Gly His Gln His Ala Gln Ser Gln Gly Leu Phe Gln Ala Leu
            195                 200                 205

Glu Cys Asn Pro Thr Leu Gln Ile Gly Tyr Asn Pro Val Gly Ser Asp
            210                 215                 220

Gln Val Ser Ala Ile Thr His Ala Thr Gln Gln Val His Gly Phe Ile
225                 230                 235                 240

Pro Gly Trp Met Leu
                245

<210> SEQ ID NO 5
<211> LENGTH: 245
<212> TYPE: PRT
<213> ORGANISM: Aspen

<400> SEQUENCE: 5

Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Asn Arg Gly Lys Leu Tyr Glu Phe Cys Ser Thr Ser Asn Met Leu
    50                  55                  60

Lys Thr Leu Glu Arg Tyr Gln Lys Cys Ser Tyr Gly Ala Glu Glu Val
65                  70                  75                  80

Asn Lys Pro Ala Lys Glu Leu Glu Asn Ser Tyr Arg Glu Tyr Leu Lys
                85                  90                  95

Val Lys Ala Arg Phe Glu Ala Leu Gln Arg Thr Gln Arg Asn Leu Leu
            100                 105                 110

Gly Glu Asp Leu Gly Pro Leu Asn Thr Lys Asp Leu Glu Gln Leu Glu
            115                 120                 125

Arg Gln Leu Glu Ser Ser Leu Asn Gln Val Arg Ser Thr Lys Thr Gln
130                 135                 140

Tyr Met Leu Asp Gln Leu Ala Asp Leu Gln Asn Lys Glu His Leu Leu
145                 150                 155                 160

Leu Glu Ala Asn Arg Gly Leu Thr Ile Lys Leu Asp Glu Ile Ser Ala
                165                 170                 175

Arg Asn Ser Leu Arg Pro Ser Trp Glu Gly Asp Asp Gln Gln Asn Met
            180                 185                 190

Ser Tyr Gly His Gln His Ala Gln Ser Gln Gly Leu Phe Gln Ala Leu
            195                 200                 205
```

```
Glu Cys Asn Pro Thr Leu Gln Ile Gly Tyr Asn Ala Val Gly Ser Asp
    210                 215                 220

Gln Val Ser Ala Ile Thr His Ala Thr Gln Gln Val His Gly Phe Ile
225                 230                 235                 240

Pro Gly Trp Met Leu
                245

<210> SEQ ID NO 6
<211> LENGTH: 29
<212> TYPE: DNA
<213> ORGANISM: Aspen

<400> SEQUENCE: 6
gttaaggaat atggggagag gtagagtgg                                   29

<210> SEQ ID NO 7
<211> LENGTH: 31
<212> TYPE: DNA
<213> ORGANISM: Aspen

<400> SEQUENCE: 7
gtccctggct aaagttctga aatccagcca c                                31

<210> SEQ ID NO 8
<211> LENGTH: 29
<212> TYPE: DNA
<213> ORGANISM: Aspen

<400> SEQUENCE: 8
gatagagaac aagataaaca ggcaggtga                                   29

<210> SEQ ID NO 9
<211> LENGTH: 24
<212> TYPE: DNA
<213> ORGANISM: Aspen

<400> SEQUENCE: 9
gttcctctga gttcgttgta gggc                                        24

<210> SEQ ID NO 10
<211> LENGTH: 23
<212> TYPE: DNA
<213> ORGANISM: Aspen

<400> SEQUENCE: 10
caagatttga ggccctacaa cga                                         23

<210> SEQ ID NO 11
<211> LENGTH: 31
<212> TYPE: DNA
<213> ORGANISM: Aspen

<400> SEQUENCE: 11
gtccctggct aaagttctga aatccagcca c                                31
```

APPLICATION OF ASPEN MADS-BOX GENES TO ALTER REPRODUCTION AND DEVELOPMENT IN TREES

STATEMENT REGARDING FEDERALLY SPONSORED RESEARCH OR DEVELOPMENT

This invention was made with government supported USDA-FRA grant.

CROSS-REFERENCE TO RELATED APPLICATIONS

Not Applicable.

TECHNICAL FIELD

The present invention relates to the production of genetically altered plants having modified characteristics such as conversion of axillary meristem to floral meristem; accelerated and earlier flowering; increased fruit production; increased nut production; increased seed output; increased branching; increased flower production; increased fruit yield; increased flower yield and combinations thereof obtained when the floral reproductive gene product PtM3 or its homolog PtM4 are over-expressed in the plant reproductive tissues. Furthermore, when the floral reproductive gene product PtM3 or its homolog PtM4 are under-expressed in a plant complete sterility; partial sterility; reduced pollen production, decreased flowering, increased biomass and combinations thereof can be obtained.

BACKGROUND OF THE INVENTION

An enormous amount of effort has been expended in attempts to elucidate the underlying mechanisms controlling flower development in various dicotyledonous plant species (reviewed in Coen, *Annu. Rev. Plant Physiol. Plant Mol. Biol.* 42:241–279, 1991; and Gasser, *Annu. Rev. Plant Physiol. Plant Mol. Biol.* 42:621–649, 1991), leading to the isolation of a family of genes which encode certain regulatory proteins. The most studied plant regulatory proteins identified to date include AGAMOUS (AG) (Yanofsky et al., *Nature* 346:35–39, 1990), APETELA I (API) (Mandel et al., *Nature* 360:273–277, 1992), and APETALA 3 (AP3) (Jack et al., *Cell* 68:683–697, 1992) in *Arabidopsis thaliana*, and DEFICIENS A (DEF A) (Sommer et al., *EMBO J.* 11:251–263, 1990), GLOBOSA (GLO) (Trobner et al., *EMBO J.* 11:4693–4704, 1992), SQUAMOSA (SQUA) (Huijser et al., *EMBO J.* 11:1239–1249, 1992), and PLENA (PLE) (Bradley et al., *Cell* 72:85–95, 1993) in *Antirrhinum majus*.

Sequence analysis of these plant regulatory genes has revealed that their gene products contain a conserved MADS-box region (Bradley et al., *Cell* 72:85–95, 1993; Huijser et al., *EMBO J.* 11:1239–1249, 1992; Jack et al., *Cell* 68:683–697, 1992; Mandel et al., *Nature* 360:273–277, 1992; Sommer et al., *EMBO J.* 11:251–263, 1990; Trobner et al., *EMBO J.* 11:4693–4704, 1992; Yanofsky et al., *Nature* 346:35–39, 1990). Transgenic approaches have been employed to study the functional roles of MADS-box genes (Kempin et al., *Plant Physiol.* 103:1041–1046, 1993; Mandel et al., *Cell* 71:133–143, 1992). MADS-box genes have been found to play an important role in specifying floral meristems and floral organ identity in plants such as *Arabidopsis* (Yanofsky et al., *The Plant Cell*, 7:721–733, 1995). Furthermore, using conserved MADS-box regions as probes, MADS-box genes have been isolated from other species including tomato (Mandel et al., *Cell* 71:133–143, 1992), tobacco (Kempin et al., *Plant Physiol.* 103:1041–1046, 1993), petunia (Angenent et al., *Plant Cell* 4:983–993, 1992), *Brassica napus* (Mandel et al., *Cell* 71:133–143, 1992), and maize (Schmidt et al., *Plant Cell* 5:729–737, 1993).

However, very few MADS-box genes have been cloned from tree species. MADS-box genes were recently found in spruce trees to encode transcription factors, which are key components in the developmental control systems of conifers, such as the identity of the floral organs (Tandre, et al., *The Plant Journal* 15(5), 615–623, 1998). Also, recently another MADS-box gene, a DEFICIENS homolog and its promoter were isolated from the dioecious tree, black cottonwood and were found to regulate expression in female and male floral meristems of the two-whorled, unisexual flowers (Strauss et al., *Plant Physiology* 124:627–639, 2000).

In addition, genetic engineering is slowly showing potential for the improvement of qualitative and quantitative traits in plants and trees. However, the full potential of transgenic plants can not be realized until methods can be developed to restrict or eliminate long distance migration of seeds and pollen from transgenic plants. Accordingly, to facilitate the production of genetically engineered trees, it is desirable that the trees be completely reproductively sterile. The ability to produce sterile transgenic trees is very desirable because there is a high potential for escape of transgenes in trees into wild populations due to their long distance movement of seeds, pollen, and their ubiquitous wild relatives. Engineering total male and female sterility for gene containment and other desired traits or partial sterility for selective breeding as discussed herein below is an important characteristic for transgenic plants to possess. It would therefore be highly desirable to have means to affect complete or partial reproductive sterility. The present invention satisfies this need and provides related advantages as well.

Also, timing of the transition from vegetative growth to flowering is one of the most important steps in plant development. This determines quality and quantity of most crop species since the transition determines the balance between vegetative and reproductive growth. It would therefore be highly desirable to have means to affect the timing of this transition so that flowering time can be controlled resulting in earlier flowering and conversion of axillary meristems to floral meristems.

Furthermore, traditionally, plant breeding involves generating hybrids of existing plants, which are examined for improved yield or quality. The improvement of existing plant crops through plant breeding is central to increasing the amount of food grown in the world since the amount of land suitable for agriculture is limited. For example, the development of new strains of crops, fruit and nuts through plant breeding has increased the yield of these crops grown in underdeveloped countries. Unfortunately, plant breeding is inherently a slow process since plants must be reproductively mature before selective breeding can proceed. For some plant species, the length of time needed to mature to flowering is so long that selective breeding, which requires several rounds of backcrossing progeny plants with their parents, is impractical. For example, some trees do not flower for several years after planting. It would therefore be highly desirable to have means to affect breeding of such plant species for a variety of different economically valuable or aesthetically pleasing traits.

SUMMARY OF THE INVENTION

The present invention provides compositions and methods for producing transgenic plants with altered characteristics by increasing the PtM3 promoter activity, or a functionally equivalent fragment of the PtM3 promoter, increasing expression of the PtM3 protein, or a functionally equivalent fragment of the PtM3 protein sequence, and combinations thereof, the resulting transgenic plants comprising at least one of the following plant characteristics which include the ability to convert axillary meristem to floral meristem; to produce accelerated flowering, i.e., earlier flowering, to increase fruit production; to increase nut production; to increase seed output; to increase branching; to increase flower production; to increase fruit yield; and to increase flower yield.

The present invention also provides compositions and methods for producing transgenic plants by suppressing the PtM3 promoter activity or a functionally equivalent fragment of the PtM3 promoter; suppressing expression of the PtM3 protein or a functionally equivalent fragment of the PtM3 protein sequence; expressing a known cytotoxic gene product under the transcriptional control of the PtM3 promoter or a functionally equivalent fragment of the PtM3 promoter; and combinations thereof, the resulting transgenic plants comprising either complete sterility or partial sterility; and wherein at least one of the effects of the sterility is reduced pollen production; decreased flowering; increased biomass and combinations thereof.

The present invention further provides compositions and methods for producing sterile transgenic plants, by suppressing the PtM3 promoter activity or a functionally equivalent fragment of the PtM3 promoter; suppressing expression of the PtM3 protein or a functionally equivalent fragment of the PtM3 protein sequence; expressing a known cytotoxic gene product under the transcriptional control of the PtM3 promoter or a functionally equivalent fragment of the PtM3 promoter; and combinations thereof, wherein additional exogenous nucleotide sequences that alter plant characteristics may be introduced into the genome of the plant, and wherein the altered plant characteristic includes at least one of increased wood quality, increased growth, increased pesticide resistance, increased herbicide resistance, and combinations thereof.

The present invention also provides kit for producing transgenic plants by increasing the PtM3 promoter activity, or a functionally equivalent fragment of the PtM3 promoter, increasing expression of the PtM3 protein, or a functionally equivalent fragment of the PtM3 protein sequence, and combinations thereof, the resulting transgenic plants comprising at least one of the following plant characteristics which include the ability to convert axillary meristem to floral meristem; to produce accelerated flowering, i.e., earlier flowering; to increase fruit production; to increase nut production; to increase seed output; to increase branching; to increase flower production; to increase fruit yield; and to increase flower yield, wherein the kit may include the following components: a purified antibody to at least one of PtM3 and PtM4 proteins or functionally equivalent fragments thereof, gene constructs containing at least a promoter (i.e., either constitutive, tissue-specific, or temporal-specific) and a coding region, containing the PtM3 polypeptide or a functionally equivalent fragments thereof, host cells, and appropriate controls.

The present invention provides kit for producing transgenic plants by suppressing the PtM3 promoter activity or a functionally equivalent fragment of the PtM3 promoter; suppressing expression of the PtM3 protein or a functionally equivalent fragment of the PtM3 protein sequence; expressing a known cytotoxic gene product under the transcriptional control of the PtM3 promoter or a functionally equivalent fragment of the PtM3 promoter; and combinations thereof, resulting in transgenic plants that may comprise either complete sterility or partial sterility; wherein at least one of the effects of the sterility is reduced pollen production; decreased flowering; increased biomass and combinations thereof; wherein the kit may include the following components: a purified antibody to at least one of PtM3 and PtM4 proteins or functionally equivalent fragments thereof, gene constructs containing at least a promoter (i.e., either constitutive, tissue-specific, or temporal-specific) and a coding region, containing the PtM3 polypeptide or a functionally equivalent fragments thereof, host cells, and appropriate controls.

The present invention provides kit for producing sterile transgenic plants by suppressing the PtM3 promoter activity or a functionally equivalent fragment of the PtM3 promoter; suppressing expression of the PtM3 protein or a functionally equivalent fragment of the PtM3 protein sequence; expressing a known cytotoxic gene product under the transcriptional control of the PtM3 promoter or a functionally equivalent fragment of the PtM3 promoter; and combinations thereof, wherein additional exogenous nucleotide sequences that alter plant characteristics may be introduced in the genome of the plant, wherein the altered plant characteristic includes at least one of increased wood quality, increased growth, increased pesticide resistance, increased herbicide resistance, and combinations thereof; wherein the kit may include the following components: a purified antibody to at least one of PtM3 and PtM4 proteins or functionally equivalent fragments thereof, gene constructs containing at least a promoter (i.e., either constitutive, tissue-specific, or temporal-specific) and a coding region, containing the PtM3 polypeptide or a functionally equivalent fragments thereof, host cells, and appropriate controls.

The present invention also provides a method of growing trangenically engineered plants in space. Plants grown extraterrestrially are insensitive to photoperiod and temperature for flowering. Transgenic plants carrying the PtM3 gene would be expected to flower in the extremely abnormal growth conditions found in a space shuttle or space station.

The patents, references and articles cited herein are hereby fully incorporated by reference. In the case of conflict between the present disclosure and the incorporated patents, references and articles, the present disclosure should control.

The foregoing and other aspects of the invention will become more apparent from the following detailed description and accompanying drawings.

BRIEF DESCRIPTION OF THE DRAWINGS

FIG. 1 illustrates the polynucleotide (SEQ ID NO:1) sequence and amino acid (SEQ ID NO:4) sequence of Aspen PtM3.

FIG. 2 illustrates the polynucleotide (SEQ ID NO:2) sequence and amino acid (SEQ ID NO:5) sequence of Aspen PtM4.

FIG. 3 illustrates the predicted amino acid sequence alignment between Aspen PtM3 (SEQ ID NO: 4) and Aspen PtM4 (SEQ ID NO: 5), wherein the sequence identity between the two homologs is 97% using the Clustal W sequence alignment algorithm. Clustal W is a general purpose multiple sequence alignment program for DNA or proteins. It produces biologically meaningful multiple sequence alignments of divergent sequences. It calculates the best match for the selected sequences, and lines them up so that the identities, similarities and differences can be seen. Details of algorithms, implementation and useful tips on usage of Clustal programs can be found in the following publications; Jeanmougin, F., Thompson, J. D., Gouy, M., Higgins, D. G. and Gibson, T. J. (1998) Multiple sequence alignment with Clustal X. Trends *Biochem Sci,* 23, 403–5. Thompson, J. D., Gibson, T. J., Plewniak, F., Jeanmiougin, F. and Higgins, D. G. (1997) The Clustal X windows interface: flexible strategies for multiple sequence alignment aided by quality analysis tools. *Nucleic Acids Research,* 24:4876–4882. Higgins, D. G., Thompson, J. D. and Gibson, T. J. (1996) Using CLUSTAL for multiple sequence alignments. *Methods Enzymol.,* 266, 383–402.

[*Populus tremuloides*] PTM1; PTM2; PtM3; PtM4: *[Populus balsamifera* subsp. *trichocarpa*] PtAG2, AAC06238.1; PtAG1, AAC06237.1; PtD, AAC13695.2: *[Antirrhinum majus]* DEFA, S12378; GLO, Q03416; SQUA, S20886; DEFH125, T17029; DEFH72, S71756; DEFH49, S78015: *[Arabidopsis thaliana]* AG, P17839; AGL1/SHP1, CAB88295; AGL2/SEP1, T51409; AGL3, S57793; AGL4/SEP2, D39534; AGL5, E39534; AGL6, F39534; AGL8, S71208; AGL9/SEP3, T00656; AGL11, T04000; AGL12, AAF23331; AGL13, T47904; AGL14, T09347; AGL15, S71200; AGL17, T05621; AGL18, AAG37900; AGL19, AAG37901; AGL20, AAG16297; AGL24, T05580; AGL27-I, AAG37902; AGL27-II, AAG37903; AGL29, T02331; AGL31, AAG37904; AP1/ AGL7, P35631; AP3, A42095; PI, A53839; *[Brassica napus]* AGL15-1, T07867; AGL15-2, T07869; *[Eucalyptus grandis]* EGM1, AAC78282; EGM2, AAC78283; EGM3, AAC78284; EAP2L, AAG30923; EAP2S, AAG27459; EAP1, AAG24909: *[Malus domestica]* MDM1, AAC25922; MDM2, AAC83170; MDM3, AAD51422; MDM4, AAD51423; MDM5, CAA04321; MDM6, CAA04322; MDM7, CAA04324; MDM8, CAA04919; MDM9, CAA04920; MDM10, CAA04324: *[Petunia hybrida]* PAG, Q40885; FBP1, JQ1689; FBP2, JQ1690; TM6, AAF73933: *[Nicotiana tabacum]* NtDEF, CAA65288; NtGLO, Q03416; NtM1, S46526; NtM4, AAF76381; NtM5, AAD39035; NtAG1, Q43585: *[Lycopersicon esculentum]* TAG1, T07185; TDR3, S23729; TDR5, CAA43170; TDR6, S23731.

FIG. 5 illustrates the polynucleotide sequence of the PtM3 Promoter (SEQ ID NO: 3) along with the 5'-untranslated region (UTR) and intron sequence. The PtM3 promoter (See bolded sequence from 1153 to 1441) contains a MADS-box sequence motif, which is believed to regulate gene expression by binding to sites, known as CArG boxes, TATA sequences, etc., present in the promoter regions of plant MADS-box genes (Riechmann et al., Biol. Chem. 378: 1079–1101 (1998).

Figure 6:
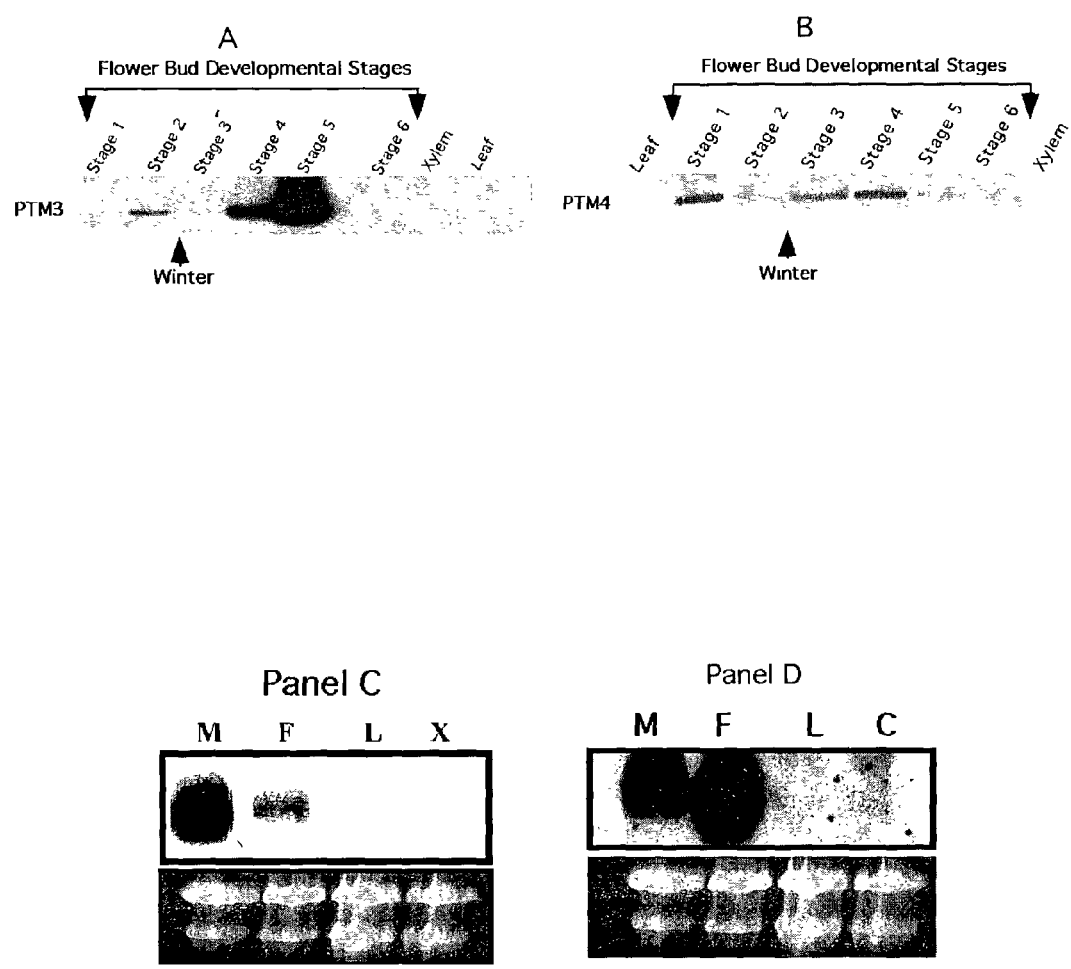

FIG. 6 illustrates the flower specific mRNA expression of PtM3 and PtM4. RNA (10 µg) from each developmental stage of female aspen flowers was fractionated on a 1.2% formaldehyde agarose gel and transferred to Hybond™ N-nylon membranes (purchased from Amersham). The blot was hybridized to $^{32}$P-labeled probe at 68° C. and washed at high stringency. The specific 3'UTR of PtM3 was used as a probe. Panel A shows expression of PtM3 mRNA at specific flower bud developmental stages, as compared to control tissues (leaf and xylem RNA). Panel B shows expression of PtM4 mRNA at specific flower bud developmental stages, as compared to control tissues (leaf and xylem RNA). Panel C shows the differential expression of male PtM3 (M) and female (F) PtM4 floral buds from stage 4 as compared to leaf (L) and xylem (X) RNA. Panel D shows the result of having the 3'-UTR probe of PtM3 used to hybridize against total RNA from Stage 4 male and female buds.

Figure 7:
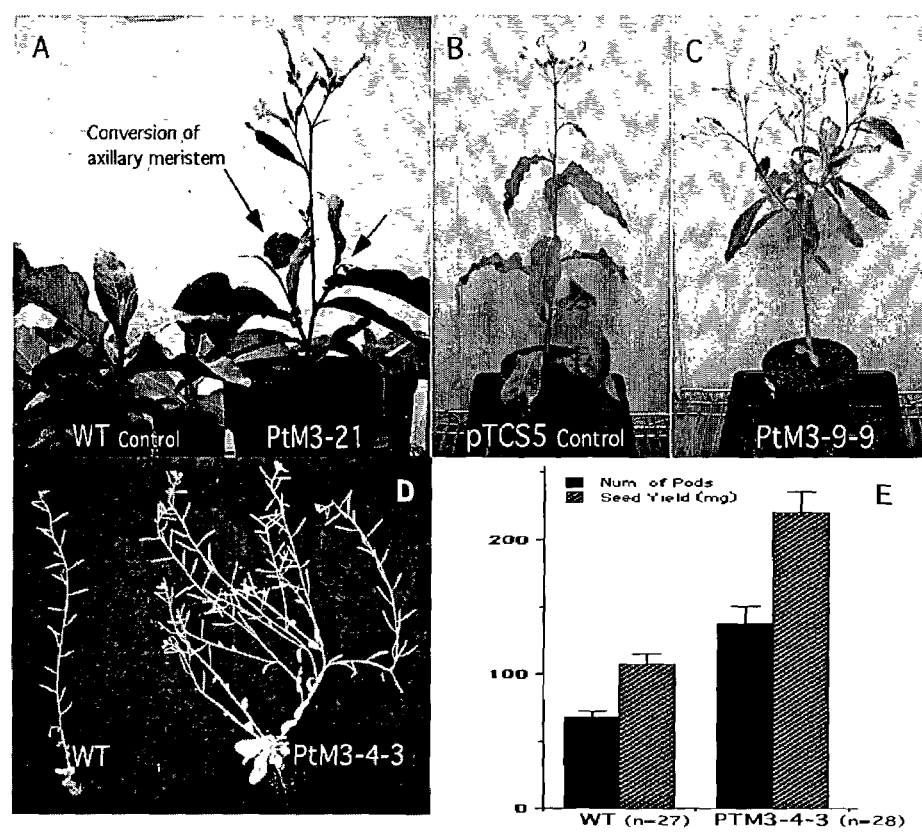

FIG. 7 illustrates the various phenotypes of transgenic plants over-expressing PtM3. Panel A, shows a tobacco plant from transgenic line PtM3-21 (right) displaying early flowering and conversion of axillary meristems to floral meristems as compared to a WT tobacco plant (left). Panel B, shows a T1 generation plant from one control construct from line pTCS5. Panel C, shows a T1 generation plant from transgenic line PtM3-9-9. Panel D, shows a T3 generation transgenic *Arabidopsis* from line PtM3-4-3 (right) displaying increased branching and flower pod production as compared to WT (left). Panel E, shows a graph depicting the average seed yields (mg) in the transgenic PtM3-4-3 plants (right) as compared to WT (left).

Figure 8:
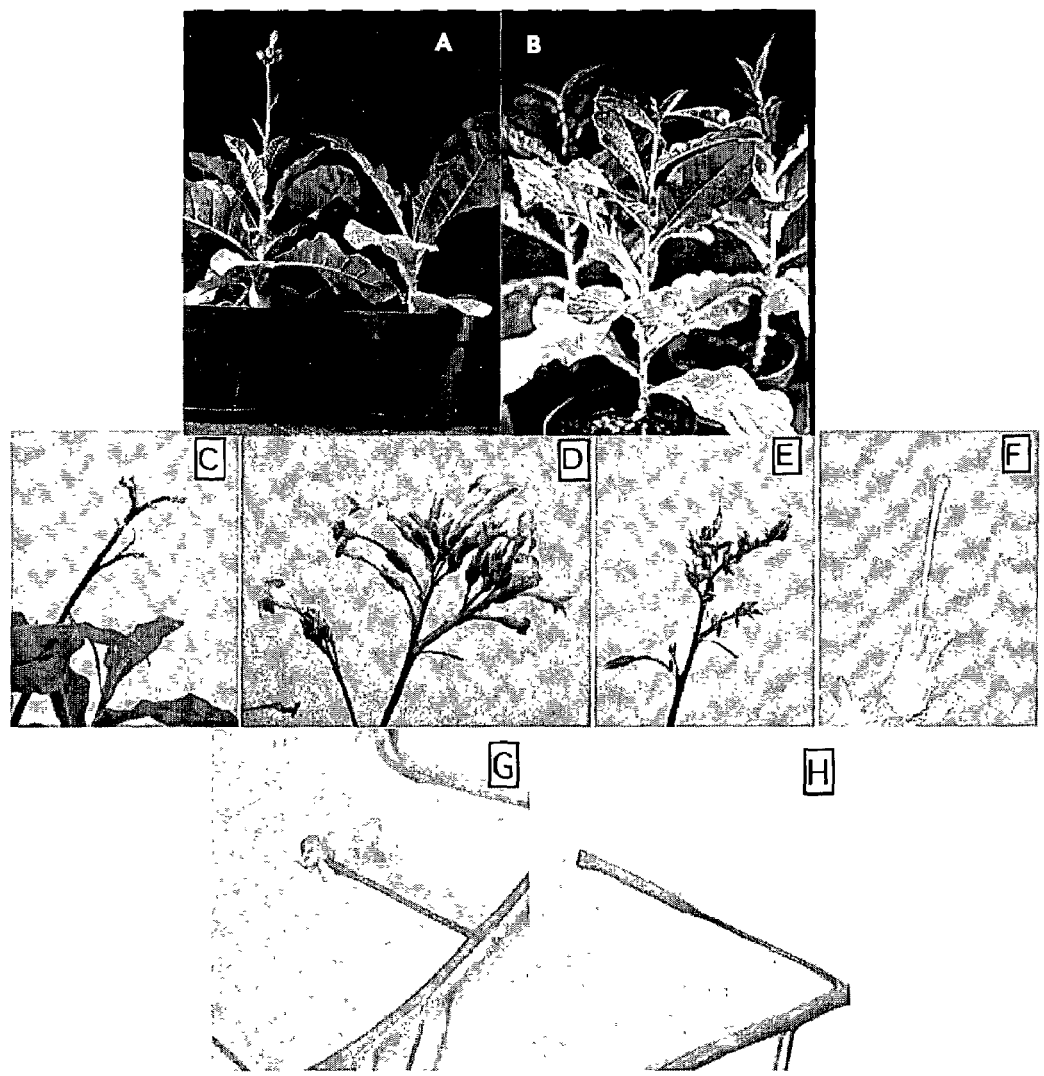

FIG. 8 illustrates transgenic plants containing antisense PtM3. In panel A, the control is flowering. In panel B, the antisense PtM3 tobacco plant is not flowering; in fact, the antisense PtM3 transgenic plants mature and begin senescing and eventually die without flowering. Panel C shows a transgenic tobacco plant containing inverted repeats of part of the PtM3 sequence which does not form flowers, in comparison to the control plants that form normal flowers (panel D). Panels E and F show the absence of petals and stamens when an inverted repeat of male PtM3 is introduced into the bisexual tobacco plant. Only female sex organs are formed and may be pollinated by pollen from a control to form pods. This shows that the PtM3 may also have a role in the male sex determination. Panel G shows flowerless *Arabidopsis* terminal and Panel H shows normal pod development in the control plant.

DETAILED DESCRIPTION OF THE INVENTION

The present invention provides compositions, methods, and kits for producing transgenic plants with a number of desirable plant characteristics. Before one can appreciate the altered plant characteristics provided herein, more detailed knowledge of the invention may be desired and follows.

A flower, like a leaf or shoot, is derived from the shoot apical meristem, which is a collection of undifferentiated cells set aside during embryogenesis. The production of vegetative structures, such as leaves or shoots, and of reproductive structures, such as flowers, is temporally segregated, such that a leaf or shoot arises early in a plant life cycle, while a flower develops later. The transition from vegetative to reproductive development is the consequence of a process termed floral induction (Yanofsky, Ann. Rev. Plant Physiol. Plant Mol. Biol. 46:167–188 (1995), which is incorporated herein by reference).

Once induced, shoot apical meristem either persists and produces floral meristem, which gives rise to flowers, and lateral meristem, which gives rise to branches, or is itself converted to floral meristem. Floral meristem differentiates into a single flower having a fixed number of floral organs in a whorled arrangement. Dicots, for example, contain four whorls (concentric rings), in which sepals (first whorl) and petals (second whorl) surround stamens (third whorl) and carpels (fourth whorl).

Although shoot meristem and floral meristem both consist of meristemic tissue, shoot meristem is distinguishable from the more specialized floral meristem. Shoot meristem generally is indeterminate and gives rise to an unspecified number of floral and lateral meristems. In contrast, floral meristem is determinate and gives rise to the fixed number of floral organs that comprise a flower.

Genetic studies have identified a number of genes involved in regulating flower development. These genes can be classified into different groups depending on their function. Flowering time genes, for example, are involved in floral induction and regulate the transition from vegetative to reproductive growth. In comparison, the floral meristem identity genes, which are the subject matter of the present invention as disclosed herein, encode proteins that promote the conversion of shoot meristem to floral meristem in an angiosperm. In addition, floral organ identity genes encode proteins that determine whether sepals, petals, stamens or carpels are formed during floral development (Yanofsky, supra, 1995; Weigel, Ann. Rev. Genetics 29:19–39 (1995), which is incorporated herein by reference). Some of the floral meristem identity gene products also have a role in specifying floral organ identity.

Many floral identity genes may be characterized as plant MADS box genes. The plant MADS box genes generally encode proteins of about 260 amino acids including a highly conserved MADS domain of about 56 amino acids (Riechmann and Meyerowitz, Biol. Chem. 378:1079–1101 (1997), which is incorporated herein by reference). The MADS domain, which was first identified in the *Arabidopsis* AGAMOUS and *Antirrhimum majus* DEFICIENS genes, is conserved among transcription factors found in humans (serum response factor; SRF) and yeast (MCM1; Norman et al., Cell 55:989–1003 (1988); Passmore et al., J. Mol. Biol. 204: 593–606 (1988), and is the most highly conserved region of the MADS domain proteins. The MADS domain is the major determinant of sequence specific DNA-binding activity and can also perform dimerization and other accessory functions (Huang et al., The Plant Cell 8:81–94 (1996)). The MADS domain frequently resides at the N-terminus, although some proteins contain additional residues at the N-terminus to the MADS domain.

The "intervening domain" or "I-domain," located immediately at the C-terminus to the MADS domain, is a weakly conserved domain having a variable length of approximately 30 amino acids (Purugganan et al., Genetics 140:345–356 (1995)). In some proteins, the I-domain plays a role in the formation of DNA-binding dimers. A third domain present in plant MADS domain proteins is a moderately conserved 70 amino acid region denoted the "keratin-like domain" or "K-domain." Named for its similarity to regions of the keratin molecule, the structure of the K-domain appears capable of forming amphipathic helices and may mediate protein-protein interactions (Ma et al., Genes Devel. 5:484–495 (1991)). The most variable domain, both in sequence and in length, is the carboxy-terminal or "C-domain" of the MADS domain proteins. Dispensable for DNA binding and protein dimerization in some MADS domain proteins, the function of this C-domain remains unknown.

The term "ectopically expressible" is used herein to refer to a nucleic acid molecule encoding a floral reproductive gene product that can be expressed in a tissue other than a tissue in which it normally is expressed or at a time other than the time at which it normally is expressed, provided that the floral reproductive gene product is not expressed from its native, naturally occurring promoter. Ectopic expression of a floral reproductive gene product is a result of the expression of the gene coding region from a heterologous promoter or from a modified variant of its own promoter, such that expression of the floral reproductive gene product is no longer in the tissue in which it normally is expressed or at the time at which it normally is expressed. An exogenous nucleic acid molecule encoding a PtM3 or PtM4 gene product under the control of its native, wild type promoter, for example, does not constitute an ectopically expressible nucleic acid molecule encoding a floral reproductive gene product. However, a nucleic acid molecule encoding an PtM3 or PtM4 gene product under the control of a constitutive promoter, which results in expression of PtM3 or PtM4 in a tissue such as shoot meristem where it is not normally expressed, is an ectopically expressible nucleic acid molecule as defined herein.

Actual ectopic expression of a floral reproductive gene is dependent on various factors and can be constitutive, tissue-specific, temporal specific or inducible expression. For example, PtM3 or PtM4, which normally may be expressed in floral meristem, may be ectopically expressible in the terminal axillary meristem of a plant, such as an angiosperm. As disclosed herein, when a floral reproductive gene product such as PtM3 or PtM4 is ectopically expressed in floral meristem of a plant, such as in an angiosperm, the axillary meristem is converted to floral meristem and early reproductive development occurs.

As disclosed herein, an ectopically expressible nucleic acid molecule encoding a floral reproductive gene product can be, for example, a transgene encoding a floral reproductive gene product under the control of a heterologous gene regulatory element. In addition, such an ectopically expressible nucleic acid molecule may be an endogenous floral reproductive gene coding sequence that is placed under the control of a heterologous gene regulatory element. The ectopically expressible nucleic acid molecule also may be, for example, an endogenous floral reproductive gene having a modified gene regulatory element such that the endogenous floral reproductive gene is no longer subject to negative regulation by a transcription factor.

Also, an ectopically expressible nucleic acid molecule encoding a floral reproductive gene product can be expressed, as desired, either constitutively or inducibly. Such an ectopically expressible nucleic acid molecule encoding a floral reproductive gene product can be an endogenous floral reproductive gene that has, for example, a mutation in a gene regulatory element. An ectopically expressible nucleic acid molecule encoding a floral reproductive gene product also can be an endogenous nucleic acid molecule encoding a floral reproductive gene product that is linked to an exogenous, heterologous gene regulatory element that confers ectopic expression. In addition, an ectopically expressible nucleic acid molecule encoding a floral reproductive gene product can be an exogenous nucleic acid molecule that encodes a floral reproductive gene product under control of a heterologous gene regulatory element.

As used herein, the term "transgenic" refers to a plant or a tree that contains in its genome an exogenous nucleic acid molecule, which can be derived from the same or a different plant species. The exogenous nucleic acid molecule can be a gene regulatory element such as a promoter, enhancer or other regulatory element or can contain a coding sequence, which can be linked to a heterologous gene regulatory element.

The term "tree" encompasses any tree and progeny thereof. The term also encompasses parts of trees, including seed, cuttings, tubers, fruit, flowers, etc. A list of non-limiting examples of trees to which the invention may apply include hardwood trees such as *Populus* species, cottonwoods, Sweetgum, or *eucalyptus* and fruit trees such as apple, peach, nut trees such as walnuts, pecans or almonds.

The term "plant" encompasses any plant and progeny thereof. The term also encompasses parts of plants, including seed, cuttings, tubers, fruit, flowers, etc. The term "plant" also includes whole plants and portions of plants, including plant organs (e.g., roots, stems, leaves, etc). A list of non-limiting examples of plants to which the invention may apply include herbaceous plants (e.g., *Arabidopsis*, asparagus and tobacco) and crop plants (e.g., Common bean (*Phaseolus vulgaris*), Maize or corn (*Zea mays*), Pea (*Pisum sativum*), Squashes (*Cucurbita* spp.), Potato (*Solanum* spp.), Tomato (*Lycopersicon esculentum*), Groundnut or peanut (*Arachis hypogaea*), Wheat (*Triticum* spp.), Barley (*Hordeum vulgare*), Sunflower (*Helianthus annuus*), Peppers (*Capsicum annuum*), Sorghum (*Sorghum bicolor*), Rice (*Oryza sativa*), Banana & plantain (*Musa* spp. ), Cotton (*Gossypium* spp.), Cabbages, turnips, etc. (*Brassica* spp.), Soybean (*Glycine max*), Lentil (*Lens culinaris*) Alfalfa (*Medicago sativa*), Field bean (*Vicia faba*), Cowpea (*Cigna unguiculata*), Coconut (*Cocos nucifera*), Lettuce (*Lactuca sativa*), Walnut (*Juglans* spp.), Melon and cucumber (*Cucumis* spp.) Almonds and peaches (*Prunus* spp.), Olive (*Olea europea*), Grape (*Vitis* spp.), Citrus (*Citrus* spp.), Cassava (*Manihot esculentum*), Sugarcane (*Saccharum* spp.), Pigeon pea (*Cajanus cajan*), Chickpea or garbanzo (*Cicer arietinum*), Oat (*Avena sativa* spp.), Flax (*Linum usitatissimum*), and Coffee (*Coffea arabica*).

As used herein, the term "floral gene product" means a gene product (i.e., a polypeptide) that, for example, promotes conversion of axillary meristem to floral meristem in a plant e.g., an angiosperm, such as PtM3, homologs, orthologs or functionally equivalent fragments thereof. As disclosed herein in Example 5, expression of a floral reproductive gene product such as PtM3 can convert axillary meristem to floral meristem, promote early reproductive development, increase branching, increase flower pod production, and increase seed yields in an angiosperm.

Floral genes in particular are conserved among distantly related angiosperm and gymnosperm species. The conservation of floral gene products in non-flowering plants such as coniferous trees indicates that floral meristem genes can promote the reproductive development of gymnosperms as well as angiosperms.

As used herein, the term "seed plant" means an angiosperm or gymnosperm. An angiosperm is a seed-bearing plant whose seeds are borne in a mature ovary (fruit). Angiosperms are divided into two broad classes based on the number of cotyledons, which are seed leaves that generally store or absorb food. Thus, a monocotyledonous angiosperm is an angiosperm having a single cotyledon, and a dicotyledonous angiosperm is an angiosperm having two cotyledons. Angiosperms are well known and produce a variety of useful products including materials such as lumber, rubber, and paper; fibers such as cotton and linen; herbs and medicines such as quinine and vinblastine; ornamental flowers such as roses and orchids; and foodstuffs such as grains, oils, fruits and vegetables.

Angiosperms encompass a variety of flowering plants, including, for example, cereal plants, herbaceous plants (such as for example tobacco plants or *Arabidopsis* plants, etc.), crop plants, perennial plants, seed plants, leguminous plants, oilseed plants, hardwood trees, fruit-bearing plants, and ornamental flowers, which general classes are not necessarily exclusive. Cereal plants, which produce an edible grain cereal, include, for example, corn, rice, wheat, barley, oat, rye, orchardgrass, guinea grass, sorghum and turfgrass. In addition, a leguminous plant is an angiosperm that is a member of the pea family (Fabaceae) and produces a characteristic fruit known as a legume. Examples of leguminous plants include, for example, soybean, pea, chickpea, moth bean, broad bean, kidney bean, lima bean, lentil, cowpea, dry bean, and peanut. Examples of legumes also include alfalfa, birdsfoot trefoil, clover and sainfoin. An oilseed plant also is an angiosperm with seeds that are useful as a source of oil. Examples of oilseed plants include soybean, sunflower, rapeseed and cottonseed. The skilled artisan will recognize that the methods of the invention can be practiced using these or other angiosperms, as desired.

An angiosperm also can be a hardwood tree, which is a perennial woody plant that generally has a single stem (trunk). Examples of such trees include alder, ash, aspen, basswood (linden), beech, birch, cherry, cottonwood, elm, *eucalyptus*, hickory, locust, maple, oak, persimmon, poplar, sweetgum, sycamore, pecans, almonds, walnut and willow. Other trees that are encompassed by this invention are dioecious trees (sexes are on different trees), hybrid trees, bisexual trees (both female and male sexes are located on one tree), and pollen producing trees. Trees are useful, for example, as a source of pulp, paper, structural material, fuel and for maintaining biodiverse forestry in an urban setting (i.e., urban forestry).

An angiosperm also can be a fruit-bearing plant, which produces a mature, ripened ovary (usually containing seeds) that is suitable for human or animal consumption. For example, hops used for their flavoring in malt liquor are a member of the mulberry family. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, orchid, lily, tulip and chrysanthemum, snapdragon, camellia, carnation and petunia plants. The skilled artisan will recognize that the methods of the invention can be practiced using these, other angiosperms, or hybrid plants or hybrid trees thereof, as desired.

The term "gymnosperm" refers to plants that produce naked seeds, i.e., seeds that are not encased in an ovary. A specific example of a gymnosperm is *Pinus taeda* (L.) [loblolly pine]. Gymnosperms encompass four classes: cycads, ginkgo, conifers and gnetophytes. The conifers are the most widespread of living gymnosperms and frequently are cultivated for structural wood or for pulp or paper. Conifers include redwood trees, pines, firs, spruces, hemlocks, Douglas firs, cypresses, junipers and yews. The skilled artisan will recognize that the methods of the invention can be practiced with these, other gymnosperms, or hybrid plants or hybrid trees thereof, as desired.

The term "dioecious tree" refers to trees having male reproductive organs in one tree and female in another (i.e., the female and male reproductive organs are on different trees). Also, the staminate and the pistillate flowers are borne on different trees.

As used herein, the term "introducing," when used in reference to a nucleic acid molecule and a seed plant such as an angiosperm or a gymnosperm, means transferring an exogenous nucleic acid molecule into the seed plant. For example, an exogenous nucleic acid molecule encoding a floral reproductive gene product can be introduced into a seed plant by a variety of methods including Agrobacterium-mediated transformation or direct gene transfer methods such as electroporation or microprojectile-mediated transformation.

The term "transformation" refers to the transfer of a foreign gene into the genome of a host organism and its genetically stable inheritance.

Transformation methods based upon the soil bacterium Agrobacterium tumefaciens, known as "agro-infection," are useful for introducing a nucleic acid molecule into a broad range of angiosperms and gymnosperms. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. Agrobacterium-based vector is a modified form of a Ti plasmid, in which the tumor-inducing functions are replaced by nucleic acid sequence of interest to be introduced into the plant host.

Current protocols for Agrobacterium-mediated transformation employ cointegrate vectors or, suitably, binary vector systems in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available from, for example, Clontech (Palo Alto, Calif.). Methods of coculturing Agrobacterium with cultured plant cells or wounded tissue such as leaf tissue, root explants, hypocotyledons, stem pieces or tubers, for example, also are well known in the art (Glick and Thompson (eds.), Methods in Plant Molecular Biology and Biotechnology, Boca Raton, Fla.: CRC Press (1993), which is incorporated herein by reference). Wounded cells within the plant tissue that have been infected by Agrobacterium can develop organs de novo when cultured under the appropriate conditions; the resulting transgenic shoots eventually give rise to transgenic plants containing the exogenous nucleic acid molecule of interest.

Agrobacterium-mediated transformation has been used to produce a variety of transgenic seed plants (see, e.g., Wang et al. (eds), Transformation of Plants and Soil Microorganisms, Cambridge, UK: University Press (1995), which is incorporated herein by reference). For example, Agrobacterium-mediated transformation can be used to produce transgenic cruciferous plants such as Arabidopsis, mustard, rapeseed and flax; transgenic leguminous plants such as alfalfa, pea, soybean, trefoil and white clover; and transgenic solanaceous plants such as eggplant, petunia, potato, tobacco and tomato. In addition, Agrobacterium-mediated transformation can be used to introduce exogenous nucleic acids into apple, aspen, belladonna, black currant, carrot, celery, cotton, cucumber, grape, horseradish, lettuce, morning glory, muskmelon, neem, poplar, strawberry, sugar beet, sunflower, walnut and asparagus plants (see, for example, Glick and Thompson, supra, 1993). Furthermore, methods for generating transgenic plants such as Aspen are known to those skilled in the art and can be readily found in the following references: Boerjan W, Baucher M, Chabbert B, Petit-Conil M, Leple J C, Pilate G, Cornu D, Monties B, Inze D, Van Doorsselaere J, Jouanin L and Van Monatgu M, with Tsai C-J, Podila G K and Chiang V L (1997) Genetic modification of lignin biosynthesis in quaking aspen and poplar. In: Klopfenstein NB, Chun Y W, Kim M S, Ahuja M R, eds Dillon, M C, Carman R C, Eskew L G, tech eds. Micropropagation, genetic engineering and molecular biology of Populus. Gen. Tech. Rep RM-GTR-297. Fort Collins, Colo.: USDA, Forest Service, Rocky Mountain research station. pp 193–205; Karnosky, D. F., B. Sen, J. Kim, B. Xiang, X. Lu, L. Cseke, D. Dixon, J. J. Liu, G. Wyckoff, and Gopi K. Podila. 2000; Engineering reproductive sterility in forest trees. Proc. International Workshop BIO-REFOR. Nepal, 1999. pp. 7–11; Genetic engineering of Populus species to improve resistance to environmental stresses; Tsai, C. J., Podila, G. K. and Chiang, V. L., (1994) Agrobacterium-mediated transformation of quaking aspen (Populus tremuloides) and regeneration of transgenic plants. Plant Mol. Biol. 14: 94–97; Tsai C J, Popko J L, Mielke M R, Hu W J, Podila G K, Chiang V L. 1998. Suppression of O-methyltransferase gene by homologous sense transgene in quaking aspen causes red-brown wood phenotypes. Plant Physiol. 117: 101–12.

Microprojectile-mediated transformation also is a well known method of introducing an exogenous nucleic acid molecule into a variety of seed plant species. This method, first described by Klein et al., Nature 327:70–73 (1987), which is incorporated herein by reference, relies on microprojectiles such as gold or tungsten that are coated with the desired nucleic acid molecule by precipitation with calcium chloride, spermidine or PEG. The microprojectile particles are accelerated at high speed into seed plant tissue using a device such as the Biolistic™ PD-1000 (Biorad, Hercules, Calif.).

Microprojectile-mediated delivery or "particle bombardment" is especially useful to transform seed plants that are difficult to transform or regenerate using other methods. Microprojectile-mediated transformation has been used, for example, to generate a variety of transgenic seed plant species, including cotton, tobacco, corn, hybrid poplar and papaya (see, for example, Glick and Thompson, supra, 1993). The transformation of important cereal crops such as wheat, oat, barley, sorghum and rice also has been achieved using microprojectile-mediated delivery (Duan et al., Nature Biotech. 14:494–498 (1996); Shimamoto, Curr. Opin. Biotech. 5:158–162 (1994), each of which is incorporated herein by reference). A rapid transformation regeneration system for the production of transgenic plants, such as transgenic wheat, in two to three months also can be useful in producing a transgenic seed plant of the invention (European Patent No. EP 0 709 462 A2, Application number 95870117.9, filed Oct. 25, 1995, which is incorporated herein by reference). In addition to the methods for plant transformation and regeneration described above for making transgenic plants, other well-known methods can be employed.

Methods of transforming forest trees including both angiosperms and gymnosperms also are well known in the art. Transgenic angiosperms such as members of the genus

*Populus*, which includes aspens and poplars, have been generated using *Agrobacterium*-mediated transformation, for example. In addition, transgenic *Populus* and sweetgum, are of interest for biomass production and for fuel production. Transgenic gymnosperms, including conifers such as white spruce and larch, also have been obtained, for example, using microprojectile bombardment (Wang et al., supra, 1995). The skilled artisan will recognize that *Agrobacterium*-mediated transformation such as Boerjan et al., 1997; Karnosky et al., 2000; Kim, J. H. 1998; Tsai et al, 1994 and 1998; can be a very suitable method of introducing a nucleic acid molecule encoding a floral reproductive gene product into a seed plant according to the methods of the invention.

The term "converting axillary meristem to floral meristem," as used herein, means promoting the formation of flower progenitor tissue where axillary progenitor tissue otherwise would be formed in the angiosperm and gymnosperm. As a result of the conversion of axillary meristem to floral meristem, flowers form in an angiosperm or gymnosperm where axillary meristems normally would form. The conversion of axillary meristem to floral meristem can be identified using well known methods, such as scanning electron microscopy, light microscopy or visual inspection (see, for example, Mandel and Yanofsky, *Plant Cell* 7:1763–1771 (1995), which is incorporated herein by reference).

A "promoter" is a polynucleotide containing element such as a TATA box, which is capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined, for example, by mapping with nuclease S1), as well as protein binding domains (consensus sequences) responsible for the binding of RNA polymerase. Examples of promoters that can be used in the present invention include constitutive, tissue and temporal specific promoters.

A variety of plant gene promoters that are regulated in response to environmental, hormonal, chemical, and/or developmental signals, also can be used for expression of the floral reproductive genes in plant cells, including promoters regulated by: (a) heat (Ainley et al. (1993). Regulatable endogenous production of cytokinins up to "toxic" levels in transgenic plants and plant tissues. *Plant Mol. Biol.* 22:13–23.); (b) light (e.g., the pea rbcS-3A promoter (Kuhlemeier et al. (1989). *Plant Cell* 1:471.) and the maize rbcS promoter (Schaffier and Sheen (1991). *Plant Cell* 3:997.), (c) hormones, such as abscisic acid (Marcotte et al. (1989). *Plant Cell* 1:969.), (d) wounding (Siebertz et al. (1989.), *Plant Cell* 1:961.), and (e) chemicals such as methyl jasminate or salicylic acid (Gatz (1997). Chemical control of gene expression. *Ann. Rev. Plant Physiol. Plant Mol. Biol.* 48:89–108.) can also be used to regulate gene expression.

Alternatively, tissue specific promoters (i.e., root, leaf, flower, and seed for example) can be fused to the coding sequence to obtain particular expression in respective organs. (Denis et al. (1993). Expression of engineered nuclear male sterility in *Brassica napus*. *Plant Physiol.* 101: 1295–1304.) In addition, the timing of the protein expression can be controlled by using promoters such as those acting at senescencing (See, Gan and Amasino (1995), inhibition of leaf senescence by autoregulated production of cytokinin. *Science* 270:1986–1988.) or during late seed development (See, Odell et al. (1994). Seed specific gene activation mediated by the Cre/lox site-specific recombination system. *Plant Physiol.* 106:447–458). Therefore, there are a variety of different types of promoters that may be used in this invention.

The term "tissue-specific promoter" refers to a promoter which directs the expression of a gene into a specific tissue such as reproductive tissues.

The term "temporal-specific promoter" refers to a promoter which temporally directs the expression of a gene so that the gene expression in the plant can be regulated based on time i.e., seasonally.

Furthermore, an appropriate regulatory element such as a promoter may be selected depending on the desired pattern or level of expression of a nucleic acid molecule linked thereto. For example, a constitutive promoter, which is active in all tissues, would be appropriate if expression of a gene product in all plant tissues is desired. In addition, a developmentally regulated or tissue-specific or temporal-specific regulatory element can be useful to direct floral reproductive gene expression to specific tissues, for example. As discussed above, inducible expression also can be particularly useful to manipulate the timing of gene expression such that, for example, a population of transgenic plants, such as seed plants of the invention that contain an expression vector comprising a floral reproductive gene linked to an inducible regulatory element, can undergo early reproductive development at essentially the same time. Selecting the time of reproductive development can be useful, for example, in manipulating the time of crop harvest.

The term "operably linked," as used in reference to a regulatory element, such as a promoter, and a nucleic acid molecule encoding a floral reproductive gene product, means that the regulatory element confers regulated expression upon the operably linked nucleic acid molecule encoding the floral reproductive gene product. Thus, the term "operably linked", as used herein, refers to a promoter, such as for example SEQ ID NO:3 or a functionally equivalent sequence thereof, linked to a nucleic acid molecule encoding a floral reproductive gene product, such as SEQ ID NO:1 or a functionally equivalent sequence thereof, such that the promoter may increase or decrease expression of the floral reproductive gene product. It is recognized that two nucleic acid molecules that are operably linked contain, at a minimum, all elements essential for transcription, including, for example, a TATA box. One skilled in the art knows, for example, that a regulatory element that lacks minimal promoter elements can be combined with a nucleic acid molecule having minimal promoter elements and a nucleic acid molecule encoding a floral reproductive gene product such that expression of the floral reproductive gene product can be increased in the presence of the appropriate inducing agent.

The term "inducing agent," as used herein, means a substance or condition that effects increased expression of a nucleic acid molecule operably linked to a particular inducible regulatory element as compared to the level of expression of the nucleic acid molecule in the absence of the inducing agent. An inducing agent can be, for example, a naturally occurring or synthetic chemical or biological molecule such as a simple or complex organic molecule, a peptide, a protein or an oligonucleotide that increases expression of a nucleic acid molecule operably linked to a particular inducible regulatory element. Examples of such inducing agents include compounds such as copper sulfate, tetracycline or an ecdysone. An inducing agent also can be a condition such as heat manifest by a certain temperature or light of a certain wavelength.

One skilled in the art can readily determine the optimum concentration of an inducing agent needed to produce increased expression of a nucleic acid molecule operably linked to an inducible promoter in a transgenic seed plant of the invention. For conveniently determining the optimum concentration of inducing agent from a range of useful concentrations, one skilled in the art can operably link the particular inducible promoter to a nucleic acid molecule encoding a reporter gene product such as beta-glucouronidase (GUS) and assay for reporter gene product activity in the presence of various concentrations of inducing agent (see, for example, Jefferson et al., *EMBO J.* 6:3901–3907 (1987), which is incorporated herein by reference).

The nucleic acid molecules encoding floral reproductive gene products provided herein also can be useful in generating sterile transgenic seed plants and in methods of producing reproductive sterility in seed plants. The methods of the invention involve producing a reproductively sterile transgenic plant, such as a seed plant having a variety of uses including safely growing transgenic trees in close contact with interfertile wild trees, increasing wood production and reducing allergenic pollen production. A method for producing reproductive sterility in seed plants, which is useful for transgene containment, can allow, for example, the introduction of transgenic trees into the environment. Of particular concern to the introduction of transgenic trees into the environment is the possibility of enhanced "weediness" or the movement of transgenes by cross-fertilization into gene pools of wild relatives. Most commercially grown forest trees, for example, are grown in close proximity to interfertile wild populations, and gene flow within and among tree populations usually is extensive, making the probability of transgene escape from plantations of fertile transgenic trees high. Regulatory agencies have based approval of transgenic tree planting on sexual isolation of the transgenic species; for example, approval of two field tests for transgenic poplars by the Animal and Plant Health Inspection Service (APHIS) was contingent on the trees not being allowed to flower (see, for example, Strauss et al., *Molec. Breed* 1:5–26 (1995), which is incorporated herein by reference). Thus, transgene containment through, for example, the use of sterile transgenic trees is central to the usefulness of improved transgenic varieties.

Methods of producing reproductively sterile seed plants also can be useful for increasing wood production, since substantial energy and nutrients are committed to reproductive development in trees. For example, in trees such as radiata pine, white spruce, balsam fir and Douglas fir, reduced growth, as measured by height or stem volume, is correlated with the early production of cones (Strauss et al., supra, 1995). Thus, the methods of the invention, which prevent flowering or cone development, for example, by producing reproductive sterility, are useful for growing substantially larger trees, thus increasing wood production.

A method for producing reproductively sterile plants, such as seed plants, also can be useful for alleviating allergies caused by tree pollen. For example, in Japan many people suffer from allergies caused by the most commonly planted forest tree, the conifer sugi (Strauss et al., supra, 1995). The methods of the invention, therefore, can be suitable for preventing pollen formation in seed plants such as the conifer sugi.

Cosuppression, which relies on expression of a nucleic acid molecule in the sense orientation, is a well known methodology that produces coordinate silencing of the introduced nucleic acid molecule and the homologous endogenous gene (see, for example, Flavell, *Proc. Natl. Acad. Sci.*, USA 91:3490–3496 (1994), which is incorporated herein by reference). Although the mechanism of cosuppression is unknown, cosuppression is induced most strongly by a large number of transgene copies or by overexpression of transgene RNA; cosuppression also can be enhanced by modification of the transgene such that it fails to be translated. Cosuppression has been used successfully to produce sterile plants; for example, a sense nucleic acid molecule containing a full-length fbp1 coding sequence under the control of the strong CaMV 35S promoter has been introduced into petunia. Two of twenty-one transformants exhibited an abnormal phenotype and contained multiple copies of the fbp1 transgene. Furthermore, fbp1 expression was undetectable in these sterile transgenic plants, indicating that expression of endogenous fbp1 was suppressed (Angenent et al., *The Plant Journal* 4:101–112 (1993), which is incorporated herein by reference).

Antisense nucleic acid molecules, which can act by reducing mRNA translation or by increasing mRNA degradation, for example, also can suppress gene expression of diverse genes and seed plant species (see, for example, Kooter et al., *Mol, Current Opin. Biol.* 4:166–171 (1993), which is incorporated herein by reference; see also Strauss et al., supra, 1995). Antisense nucleic acid molecules previously have been used to successfully suppress the expression of a homologous endogenous gene, thereby generating sterile plants. For example, an antisense chalcone synthase gene under control of the CaMV 35S promoter with an anther-specific enhancer sequence effectively suppressed endogenous chalcone synthase expression levels, resulting in male sterility in transgenic petunia plants (Van der Meer et al., *The Plant Cell* Vol 4:253–262 (1992), which is incorporated herein by reference). Similarly, the full-length tomato TM5 MADS box gene, when placed in antisense orientation under control of the CaMV 35S promoter, was used to produce sterile transgenic tomato plants (Pnuell et al., *The Plant Cell*, Vol. 6, 175–186 (1994), which is incorporated herein by reference).

Plant reproductive sterility can also occur through other traditional molecular methods such as by fusing the promoter to a cytotoxic gene such as an RNAse gene or through using constructs with inverted repeat sequences. Gene suppression can also occur by methods such as RNA interference (RNAi), inverted repeat constructs and post-transcriptional gene silencing (PTGS) processes in which double-stranded (ds) RNA induces the degradation of homologous RNA sequences. In plants, transcriptional gene silencing resulting from sequence homology in promoter regions has also been observed and correlated with increased promoter methylation. (Kooter et al., *Trends Plant Sci.*, 4, 340–346 (1999).

Plant gene suppression may also result in delayed reproductive growth. The delayed reproductive may increase the length of the vegetative growth stage and cause the plants to grow faster, since the energy used for development of flowers and seeds can be saved for vegetative growth. Thus, delaying or eliminating reproductive growth results in a higher yield of vegetable species such as spinach, radish, cabbage, or tree species. In addition, such plants will be more desirable for as garden and street species, since their production of pollen allergens can be reduced or eliminated The methods of the invention for producing reproductive sterility rely upon introducing into the genome of a seed plant one or more sense or antisense nucleic acid molecules encoding a floral reproductive gene product, or a functionally equivalent fragment thereof, such that expression of PtM3, homolog or ortholog gene products, including expression of endogenous PtM3 or homolog gene products, is suppressed in the transgenic seed plant. The skilled artisan will recognize that effective suppression of endogenous PtM3 or homolog gene product expression depends upon the one or more introduced nucleic acid molecules having a high percentage of homology with the corresponding endogenous gene loci.

A highly homologous nucleic acid molecule is highly suitable in the methods of the invention. However, a sense or antisense nucleic acid molecule encoding only a fragment of PtM3 or its homolog coding sequence, can be useful in performing the methods of the invention and achieving plant suppression. For example, leaf-specific inhibition of GUS gene expression in transgenic tobacco plants using an antisense RNA with a 41-base homology spanning the translation start codon of the gene has been shown. (Cannon et al., *Plant Mol. Bio.,* 15:39–47 (1990).

As used herein in reference to a nucleic acid molecule encoding a floral reproductive gene product, the terms "sense" and "antisense" have their commonly understood meanings.

As used herein in reference to a nucleic acid molecule encoding a floral reproductive gene product, the term "fragment" means a portion of the nucleic acid sequence containing at least about 50 base pairs to the full-length of the nucleic acid molecule encoding the floral reproductive gene product. In contrast to an active fragment or a functionally equivalent fragment, as defined herein, a fragment of a nucleic acid molecule encoding a floral reproductive gene product need not encode a functional portion of a gene product. A fragment may also be a portion of the nucleic acid that is less than full-length and comprises at least a minimum length capable of hybridizing specifically with an PtM3 nucleic acid according to the present invention (or a sequence complementary thereto) under stringent conditions as defined below. The length of such a fragment is suitably 15 nucleotides or more, although a shorter nucleic acid can be employed as a probe or primer if it is shown to specifically hybridize under stringent conditions with a target nucleic acid by methods well known in the art.

In the methods of the invention for producing reproductive sterility, the sense or antisense nucleic acid molecule is expressed under control of a strong promoter that is expressed, at least in part, in floral meristem. The constitutive cauliflower mosaic virus 35S promoter (Odell et al., supra, 1985), for example, or other strong promoters as disclosed herein, can be useful in the methods of the invention. In addition, an RNA polymerase III promoter can be useful in methods of producing reproductive sterility using an antisense nucleic acid molecule (see, for example, Bourque and Folk, *Plant Mol. Biol.* 19:641–647 (1992), which is incorporated herein by reference).

As used herein, the term "heterologous regulatory element" means a regulatory element or a promoter derived from a different gene than the gene encoding the floral reproductive gene product to which it is operably linked. A vector containing a floral reproductive gene, however, contains a nucleic acid molecule encoding a floral reproductive gene product operably linked to a homolgous regulatory element. Such a vector does not contain a nucleic acid molecule encoding a floral reproductive gene product operably linked to a heterologous regulatory element and, thus, is not an expression vector of the invention.

A useful plant gene construct or an expression vector can contain a constitutive regulatory element for expression of an exogenous nucleic acid molecule in all or most tissues of a plant, such as a seed plant. The use of a constitutive regulatory element can be particularly convenient because expression from the element is relatively independent of developmentally regulated or tissue-specific factors. For example, the cauliflower mosaic virus 35S promoter (CaMV 35S) is a well-characterized constitutive regulatory element that produces a high level of expression in all plant tissues (Odell et al., *Nature* 313:810–812 (1985), which is incorporated herein by reference). Furthermore, the CaMV 35S promoter can be particularly useful due to its activity in numerous different seed plant species (Benfey and Chua, *Science* 250:959–966 (1990), which is incorporated herein by reference; Odell et al., supra, 1985). Other constitutive regulatory elements useful for expression in a seed plant include, for example, the cauliflower mosaic virus 19S promoter; the Figwort mosaic virus promoter (Singer et al., *Plant Mol. Biol.* 14:433 (1990), which is incorporated herein by reference); and the nopaline synthase (nos) gene promoter (An, *Plant Physiol.* 81:86 (1986), which is incorporated herein by reference).

In addition, an expression vector of the present invention can contain a regulated gene regulatory element such as a promoter or enhancer element. A particularly useful regulated promoter is a tissue-specific or a temporal-specific promoter such as the PtM3 promoter which is both a tissue-specific and temporal-specific promoter. Another example of a regulated promoter is a shoot meristem-specific CDC2 promoter (Hemerly et al., *Plant Cell.* 5:1711–1723 (1993), which is incorporated herein by reference).

As used herein in reference to a particular nucleic acid molecule or polynucleotide or gene product (i.e., polypeptide), the term "substantially purified" means that the particular nucleic acid molecule or gene product is in a form that is relatively free from contaminating lipids, unrelated gene products, unrelated nucleic acids or other cellular material normally associated with the particular nucleic acid molecule or gene product in a cell.

An "active fragment" or a "functionally equivalent fragment" refers to a portion of a gene or a gene product that contains the essential sequences, such as the active site motif, which provides the sequence fragment with the ability to perform essentially the same function as the full-length gene or the gene product. An active fragment incorporated into the genome of a plant can be identified by phenotypic analysis of the plant which ectopically expresses the active fragment producing early flowering, etc. For analysis of a large number of active fragments of a PtM3 or its homolog, nucleic acid molecules encoding the active fragments can be assayed in pools, and active pools subsequently subdivided to identify the active nucleic acid molecule.

The term "functional portion" or "functional fragment" or "functional equivalent" of an enzyme is that portion, fragment, or equivalent which contains the active site for binding one or more reactants or is capable of improving or regulating the rate of reaction. The active site may be made up of separate portions present on one or more polypeptide chains and will generally exhibit high substrate specificity.

As used herein, the term "variant" covers any sequence which exhibits at least about 75%, more suitably at least about 80% and, more suitably yet, at least about 90% identity to a sequence of the present invention. Sequence variants include not only genetically engineered sequence variants, but also naturally occurring variants that arise e.g., within *Populus* populations, including allelic variants and polymorphisms, as well as variants that occur in different genotypes and plant species. Most suitably, a "variant" is any sequence which has at least about a 99% probability of being the same as the inventive sequence. Such probability for DNA sequences is measured by the computer algorithm FASTA (version 2.0u4, February 1996; Pearson W. R. et al., *Proc. Natl. Acad. Sci.*, 85:2444–2448, 1988), the probability for translated DNA sequences is measured by the computer algorithm TBLASTX and that for protein sequences is measured by the computer algorithm BLASTP (Altschul, S. F. et al. *J. Mol. Biol.*, 215:403–410, 1990). The term "variants" thus encompasses sequences wherein the probability of finding a match by chance (smallest sum probability) in a database, is less than about 1% as measured by any of the above tests.

The term a "function-conservative variant" refers to a polypeptide (or a polynucleotide encoding the polypeptide) having a given amino acid residue that has been changed without altering the overall conformation and function of the polypeptide, including, but not limited to, replacement of an amino acid with one having similar physico-chemical properties (such as, for example, acidic, basic, hydrophobic, and the like). Amino acids with have similar physico-chemical properties are well known in the art. For example, arginine, histidine and lysine are hydrophilic-basic amino acids and may be interchangeable. Similarly, isoleucine, a hydrophobic amino acid, may be replaced with leucine, methionine or valine.

As used herein, the term "functionally equivalent variant of PtM3 or its homolog" encompasses an active segment of PtM3 or its homolog, which is a polypeptide portion of a PtM3 or its homolog that, when ectopically expressed, alters normal reproductive plant or tree development such that altered plant or tree properties are produced. An active fragment can be, for example, an amino terminal, internal or carboxy terminal fragment of Aspen PtM3 (SEQ ID NO:4) that, when ectopically expressed in a plant, alters normal reproductive development such that plants with altered reproductive capacity are produced. An active fragment of a PtM3 gene product can include, for example, the MADS domain and can have the ability to bind DNA specifically. The skilled artisan will recognize that a nucleic acid molecule encoding an active segment of PtM3 gene product can be used to generate a plant of the invention characterized by producing early flowering, etc. and in the related methods and kits of the invention described further below.

The term "oligonucleotide" refers to a nucleic acid, generally of at least 10, suitably at least 15, and more suitably at least 20 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as polymerase chain reaction (PCR) primers, either for cloning full length or a fragment of PtM3, or to detect the presence of nucleic acids encoding PtM3. In a further embodiment, an oligonucleotide of the present invention can form a triple helix with a PtM3 DNA molecule. In still another embodiment, a library of oligonucleotides arranged on a solid support, such as a silicon wafer or chip, can be used to detect various polymorphisms of interest. Generally, oligonucleotides are prepared synthetically, suitably on a nucleic acid synthesizer. Accordingly, oligonucleotides can be prepared with non-naturally occurring phosphoester analog bonds, such as thioester bonds, etc.

The term "non-coding region" refers to that portion of the gene that does not directly encode a polypeptide. The boundaries of the non-coding region are located before the start codon and after the stop codon. The non-coding region includes the untranslated regions of the genomic DNA.

Also, as used herein, the term "gene" refers to a nucleic acid fragment that expresses a specific protein including the regulatory sequences preceding (5' noncoding) and following (3' noncoding) the coding region. "Native" gene refers to the gene as found in nature with its own regulatory sequences.

The term "endogenous gene" refers to the native gene normally found in its natural location in the genome.

"Exogenous" refers to biological material, such as a polynucleotide or protein, that has been isolated from a cell and is then introduced into the same or a different cell. For example, a polynucleotide encoding a PtM3 gene of the invention can be cloned from xylem cells of a particular species of tree, inserted into a plasmid and reintroduced into xylem cells of the same or different species.

The term "transgene" refers to a homologous or heterologous gene that is introduced by gene transfer methods disclosed herein into the cell, tissue or organ of a host organism. The term "transgenic" or "transformed" when referring to a cell or organism, also includes (1) progeny of the cell or organism and (2) plants produced from a breeding program employing such a "transgenic" plant as a parent in a cross and exhibiting an altered phenotype resulting from the presence of the recombinant PtM3 gene construct.

The term "PtM3 polypeptide" refers to a protein encoded by an PtM3 gene, including alleles and homologs of PtM3, functionally equivalent fragments, or by a variant of the PtM3 gene, having PtM3 biological activity. An PtM3 polypeptide can be isolated from a natural source, produced by the expression of a recombinant PtM3 nucleic acid, or be chemically synthesized. Techniques for chemical synthesis of polypeptides are described, for example, in Merrifield, J. Amer. Chem. Soc. 85:2149–2156, 1963.

The polypeptides of the present invention can be purified by any of the means known in the art. Various methods of protein purification are described, e.g., in Guide to Protein Purification, ed. Deutscher, Meth. Enzymol. 185, Academic Press, San Diego, 1990; and Scopes, Protein Purification: Principles and Practice, Springer Verlag, New York, 1982.

Encompassed by the claimed PtM3 polypeptides are variant polypeptides in which there have been substitutions, deletions, insertions or other modifications of the native PtM3 polypeptide. The variants substantially retain structural and/or biological characteristics and are suitably silent or conservative substitutions of one or a small number of contiguous amino acid residues.

The native PtM3 polypeptide sequence can be modified by conventional methods, e.g., by acetylation, carboxylation, phosphorylation, glycosylation, ubiquitination, and labeling, whether accomplished by in vivo or in vitro enzymatic treatment of an PtM3 polypeptide or by the synthesis of an PtM3 polypeptide using modified amino acids.

There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Molecular Cloning: A Laboratory Manual, 2nd ed., vol. 1–3, ed. Sambrook et al., Cold Spring Harbor Laboratory Press: Cold Spring Harbor, N.Y., 1989; and Current Protocols in Molecular Biology, ed. Ausubel et al., Greene Publishing and Wiley-Interscience: New York, 1987 (with periodic updates).

The present invention also encompasses fragments of PtM3 polypeptides that lack at least one residue of a native full-length PtM3 polypeptide yet retain at least one of the biological activities characteristic of Aspen PtM3. For example, such a fragment can cause early flowering when expressed as a transgene in a host plant or possession of a characteristic immunological determinant. As an additional example, an immunologically active fragment (i.e., antigenic determinants or epitopes) of an PtM3 polypeptide is capable of raising PtM3-specific antibodies in a target immune system (e.g., murine or rabbit) or of competing with PtM3 polypeptide for binding to PtM3-specific antibodies, and is thus useful in immunoassays for the presence of PtM3 polypeptides in a biological sample. Such immunologically active fragments typically have a minimum size of 7 to 17 amino acids.

The present invention also provides fusion polypeptides including, for example, heterologous fusion polypeptides, i.e., an PtM3 polypeptide sequence or fragment thereof and a heterologous polypeptide sequence, e.g., a sequence from a different polypeptide. Such heterologous fusion polypeptides, thus, exhibit biological properties (such as ligand-binding, catalysis, secretion signals, antigenic determinants, etc.) derived from each of the fused sequences. Fusion partners include, for example, immunoglobulins, beta galactosidase, trpE, protein A, beta lactamase, alpha amylase, alcohol dehydrogenase, yeast alpha mating factor, and various signal and leader sequences which, e.g., can direct the secretion of the polypeptide. Fusion polypeptides are typically made by the expression of recombinant nucleic acids or by chemical synthesis.

The term "coding sequence" refers to that portion of the gene that contains the information for encoding a polypeptide. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences The term "encoding" and "coding" refer to the process by which a gene, through the mechanisms of transcription and translation, provides the information to a cell from which a series of amino acids can be assembled into a specific amino acid sequences to produce an active enzyme. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the present invention encompasses more than the specific exemplary sequences. Modifications to the sequences, such as deletions, insertions or substitutions in the sequence which produce silent changes that do not substantially affect the functional properties of the resulting protein molecule, are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may, in fact, be desirable to make mutants of the sequence to study the effect of retention of biological activity of the protein. Each of these proposed modifications is well within the routine skill in the art, as is the determination of retention of biological activity in the encoded products. Moreover, the skilled artisan recognizes that sequences encompassed by the present invention are also defined by their ability to hybridize, under stringent condition, with the sequences exemplified herein.

The term "expression" is meant to refer to the production of a polypeptide encoded by a gene. "Overexpression" refers to the production of a polypeptide in transgenic organisms that exceed levels of production in normal or non-transformed organisms.

The term "% identity" refers to the percentage of the nucleotides/amino acids of one polynucleotide/polypeptide that are identical to the nucleotides/amino acids of another sequence of polynucleotide/polypeptide as identified by a program such as GAP from Genetics Computer Group Wisconsin (GCG) package (version 9.0) (Madison, Wis.). GAP uses the algorithm of Needleman and Wunsch (*J. Mol. Biol.* 48: 443–453, 1970) to find the alignment of two complete sequences that maximizes the number of matches and minimizes the number of gaps. When parameters required to run the above algorithm are not specified, the default values offered by the program are contemplated.

The "% similarity" or "% homology" between two polypeptide sequences is a function of the number of similar positions shared by two sequences on the basis of the scoring matrix used divided by the number of positions compared and then multiplied by 100. This comparison is made when two sequences are aligned (by introducing gaps if needed) to determine maximum homology. PowerBlast program, implemented by the National Center for Biotechnology Information, can be used to compute optimal, gapped alignments. GAP program from Genetics Computer Group Wisconsin package (version 9.0) (Madison, Wis.) can also be used. GAP uses the algorithm of Needleman and Wunsch (*J. Mol. Biol.* 48: 443–453, 1970) to find the alignment of two complete sequences that maximizes the number of matches and minimizes the number of gaps. When parameters required to run the above algorithm are not specified, the default values offered by the program are contemplated. The following parameters are used by the GCG program GAP as default values (for polypeptides): gap creation penalty:12; gap extension penalty:4; scoring matrix:Blosum62.cpm (local data file).

A first nucleic acid is "substantially similar" to a second nucleic acid if, when optimally aligned (with appropriate nucleotide insertions or deletions) with the other nucleic acid (or its complementary strand), there is nucleotide sequence identity in at least about 75%–90% of the nucleotide bases, and suitably greater than 90% of the nucleotide bases. ("Substantial sequence complementarity" requires a similar degree of sequence complementarity.) Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

A "homolog" of the PtM3 gene is a native gene sequence isolated from a plant species other than Aspen that has at least one of the biologically activities of PtM3, e.g., affecting early flowering in transgenic plants, etc., as discussed above.

The term "ortholog" as used herein refers to orthologous genes, wherein the gene loci in different species are sufficiently similar in their nucleotide sequences to suggest that they originated from a common ancestral gene. (See Pei-Show Juo, *Concise Dictionary of Biomedicine and Molecular Biology* (CRC Press 2d ed. 2002)).

An "isolated polynucleotide" refers to a component that is removed from its original environment (for example, its natural environment if it is naturally occurring). An isolated nucleic acid or polypeptide may contains less than about 50%, suitably less than about 75%, and most suitably less than about 90%, of the cellular components with which it was originally associated. A polynucleotide amplified using PCR so that it is sufficiently and easily distinguishable (on a gel, for example) from the rest of the cellular components is considered "isolated". The polynucleotides and polypeptides of the present invention may be "substantially pure," i.e., having the highest degree of purity that can be achieved using purification techniques known in the art.

A "polynucleotide" is intended to include double or single stranded genomic and cDNA, RNA, any synthetic and genetically manipulated polynucleotide, and both sense and anti-sense strands together or individually (although only sense or anti-sense stand may be represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil. Polynucleotide also encompasses a nucleic acid, the structure of which is not identical to that of any naturally occurring nucleic acid or to that of any fragment of a naturally occurring genomic nucleic acid spanning more than three separate genes. The term, therefore, covers, for example, (a) a DNA which has the sequence of part of a naturally occurring genomic DNA molecules but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by PCR, or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

The term "vector" is a recombinant nucleic acid construct, such as a plasmid, phage, genome, virus genome, cosmid, or artificial chromosome, to which a polynucleotide of the present invention may be attached. In a specific embodiment, the vector may bring about the replication of the attached segment, e.g., in the case of a cloning vector.

The term "expression cassette" or "gene construct" refers to a polynucleotide which contains both a promoter and a protein coding sequence such that expression of a given protein is achieved upon insertion of the expression cassette into a cell.

DNA constructs incorporating an PtM3 gene or fragment thereof according to the present invention suitably place the PtM3 protein coding sequence under the control of an operably linked promoter that is capable of expression in a plant cell. Various promoters suitable for expression of heterologous genes in plant cells are known in the art, including constitutive promoters, e.g. the cauliflower mosaic virus (CaMV) 35S promoter, which is expressed in many plant tissues, organ- or tissue-specific promoters, and tissue-specific or temporal-specific promoters that direct the expression of the desired gene into specific reproductive tissue and/or at specific times of the year, for example.

Natural or synthetic nucleic acids according to the present invention can be incorporated into recombinant nucleic-acid constructs, typically DNA constructs, capable of introduction into and replication in a host cell. Usually the DNA constructs will be suitable for replication in a unicellular host, such as *E. coli* or other commonly used bacteria, but can also be introduced into yeast, mammalian, plant or other eukaryotic cells.

Suitably, such a nucleic-acid construct is a vector comprising a replication system recognized by the host. For the practice of the present invention, well-known compositions and techniques for preparing and using vectors, host cells, introduction of vectors into host cells, etc. are employed, as discussed, inter alia, in Sambrook et al., 1989, or Ausubel et al., 1987.

Methods for chemical synthesis of nucleic acids are discussed, for example, in Beaucage and Carruthers, *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

As used herein, "amplified DNA" refers to the product of, nucleic-acid amplification of a target nucleic-acid sequence. Nucleic-acid amplification can be accomplished by any of the various nucleic-acid amplification methods known in the art, including the PCR. A variety of amplification methods are known in the art and are described, inter alia, in U.S. Pat. Nos. 4,683,195 and 4,683,202 and in *PCR Protocols: A Guide to Methods and Applications*, Innis et al. eds., Academic Press, San Diego, 1990.

The term "hybridization" conditions refers to the conditions used herein for isolating a gene, for example, the conditions are relatively stringent such that non-specific hybridization is minimized. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook, supra, 1989).

Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarily over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide. See also, Sambrook et al., 1989 at 9.47–9.52, 9.56–9.58; Kanehisa, *Nuc. Acids Res.* 12:203–213, 1984; and Wetmur and Davidson, *J. Mol. Biol.* 31:349–370, 1968.

The invention also provides a kit for over-expression and suppressed expression of floral reproductive genes in plants. The kit may include at least one of the PtM3 gene, the PtM3 gene product, homologs, orthologs, functionally equivalent fragments, primers, promoters, fragments, antibodies, gene constructs, expression vectors, host cells, appropriate reagents to facilitate high efficiency transformation of a seed plant and combinations thereof; wherein the over-expression may result in plants having at least one of accelerated or early flowering; increased fruit production; increased nut production; increased seed output; increased branching; increased flower production; increased fruit yield; increased flower yield a plant, and a combination thereof and the suppressed expression may result in at least one of complete sterility; partial sterility; reduced pollen production, decreased flowering, increased biomass and combinations thereof.

If desired, a kit of the invention also can contain a plant expression vector. As used herein, the term "plant expression vector" means a self-replicating nucleic acid molecule that provides a means to transfer an exogenous nucleic acid molecule into a seed plant host cell and to express the molecule therein. Plant expression vectors encompass vectors suitable for *Agrobacterium*-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for *Agrobacterium*-mediated transformation.

In addition to containing a nucleic acid molecule encoding an PtM3 gene product operatively linked to a regulatory element, a plant expression vector of the invention can contain, if desired, additional elements. A binary vector for *Agrobacterium*-mediated transformation contains one or both T-DNA border repeats and can also contain, for example, one or more of the following: a broad host range replicon, an ori T for efficient transfer from *E. coli* to *Agrobacterium*, a bacterial selectable marker such as ampicillin and a polylinker containing multiple cloning sites.

A plant expression vector for physical transformation can have, if desired, a plant selectable marker and can be based on a vector such as pBR322, pUC, pGEM and M13, which are commercially available, for example, from Pharmacia (Piscataway, N.J.) or Promega (Madison, Wis.). In plant expression vectors for physical transformation of a seed plant, the T-DNA borders or the ori T region can optionally be included but provide no advantage.

The definition of the terms "complement", "reverse complement" and "reverse sequence", as used herein, is best illustrated by the following example. For the sequence 5' AGGACC 3', the complement, reverse complement and reverse sequence are as follows:

```
complement              3' TCCTGG 5'
reverse complement      3' GGTCCT 5'
reverse sequence        5' CCAGGA 3'.
```

Variants of the isolated sequences commercially important species utilized by the lumber industry, are contemplated. These include the following gymnosperms, by way of example: loblolly pine *Pinus taeda*, slash pine *Pinus elliotti*, sand pine *Pinus clausa*, longleaf pine *Pinus palustrus*, shortleaf pine *Pinus echinata*, ponderosa pine *Pinus ponderosa*, Jeffrey pine *Pinus jeffrey*, red pine *Pinus resinosa*, pitch pine *Pinus rigida*, jack pine *Pinus banksiana*, pond pine *Pinus serotina*, Eastern white pine *Pinus strobus*, Western white pine *Pinus monticola*, sugar pine *Pinus lambertiana*, Virginia pine *Pinus virginiana*, lodgepole pine *Pinus contorta*, Caribbean pine *Pinus caribaea*, *P. pinaster*, Calabrian pine *P. brutia*, Afghan pine *P. eldarica*, Coulter pine *P. coulteri*, European pine *P. nigra* and *P. sylvestris*; Douglas-fir *Pseudotsuga menziesii*; the hemlocks which include Western hemlock *Tsuga heterophylla*, Eastern hemlock *Tsuga canadensis*, Mountain hemlock *Tsuga mertensiana*; the spruces which include the Norway spruce *Picea abies*, red spruce *Picea rubens*, white spruce *Picea glauca*, black spruce *Picea mariana*, Sitka spruce *Picea sitchensis*, Englemann spruce *Picea engelmanni*, and blue spruce *Picea pungens*; redwood *Sequoia sempervirens*; the true firs include the Alpine fir *Abies lasiocarpa*, silver fir *Abies amabilis*, grand fir *Abies grandis*, nobel fir *Abies procera*, white fir *Abies concolor*, California red fir *Abies magnifica*, and balsam fir *Abies balsamea*, the cedars which include the Western red cedar *Thuja plicata*, incense cedar *libocedrus decurrens*, Northern white cedar *Thuja occidentalis*, Port Orford cedar *Chamaecyparis lawsoniona*, Atlantic white cedar *Chamaecyparis thyoides*, Alaska yellow-cedar *Chamaecyparis nootkatensis*, and Eastern red cedar *Huniperus virginiana*; the larches which include Eastern larch *Larix laricina*, Western larch *Larix occidentalis*, European larch *Larix decidua*, Japanese larch *Larix leptolepis*, and Siberian larch *Larix siberica*; bold cypress *Taxodium distichum* and Giant sequoia *Sequoia gigantea*; and the following angiosperms, by way of example: *Eucalyptus alba*, *E. bancroftii*, *E. botyroides*, *E. bridgesiana*, *E. calophylla*, *E. camaldulensis*, *E. citriodora*, *E. cladocalyx*, *E. coccifera*, *E. curtisii*, *E. dalrympleana*, *E. deglupta*, *E. delagatensis*, *E. diversicolor*, *E. dunnii*, *E. ficifolia*, *E. globulus*, *E. gomphocephala*, *E. gunnii*, *E. henryi*, *E. laevopinea*, *E. macarthurii*, *E. macrorhyncha*, *E. maculata*, *E. marginata*, *E. megacarpa*, *E. melliodora*, *E. nicholii*, *E. nitens*, *E. nova-angelica*, *E. obliqua*, *E. obtusiflora*, *E. oreades*, *E pauciflora*, *E. polybractea*, *E. regnans*, *E. resinifera*, *E. robusta*, *E. rudis*, *E. saligna*, *E. sideroxylon*, *E. stuartiana*, *E. tereticornis*, *E. torelliana*, *E. urnigera*, *E. urophylla*, *E. viminalis*, *E. viridis*, *E. wandoo* and *E. youmanni*.

The availability of the PtM3 gene and its sequence makes it possible to obtain homologs or orthologs of the PtM3 gene in other organisms by conventional methods, through the use of nucleic acid and antibody probes and DNA primers based on the PtM3 sequence, as described in greater detail below. For example, these probes and primers are also useful in research on the patterns of expression and structure-function relationships for Aspen PtM3 and its homologs or orthologs, and for determining the interaction of these genes with other plant genes involved in floral development.

Nucleic acid probes and primers can be prepared based on nucleic acids according to the present invention, e.g., the PtM3 gene of FIG. 1 (SEQ ID NO:1) or the PtM4 gene of FIG. 2 (SEQ ID NO:2). A "probe" comprises an isolated nucleic acid attached to a detectable label or reporter molecule well known in the art. Typical labels include radioactive isotopes, ligands, chemiluminescent agents, and enzymes.

"Primers" are short nucleic acids, suitably DNA oligonucleotides 15 nucleotides or more in length, which are annealed to a complementary target DNA strand by nucleic acid hybridization to form a hybrid between the primer and the target DNA strand, then extended along the target DNA strand by a polymerase, suitably a DNA polymerase. Primer pairs can be used for amplification of a nucleic acid sequence, e.g., by the polymerase chain reaction (PCR) or other nucleic-acid amplification methods well known in the art. PCR-primer pairs can be derived from the sequence of a nucleic acid according to the present invention, for example, by using computer programs intended for that purpose such as Primer (Version 0.5, COPYRGT. 1991, Whitehead Institute for Biomedical Research, Cambridge, Mass.).

Methods for preparing and using probes and primers are described, for example, in Sambrook et al., *Molecular Cloning: A Laboratory Manual*, 2nd ed., vol. 1–3, ed. Sambrook et al., Cold Spring Harbor Laboratory Press, Cold Spring Harbor, N.Y., 1989; *Current Protocols in Molecular Biology*, ed. Ausubel et al., Greene Publishing and Wiley-Interscience, New York, 1987 (with periodic updates); and Innis et al., *PCR Protocols: A Guide to Methods and Applications*, Academic Press: San Diego, 1990. Probes or primers can be free in solution or covalently or noncovalently attached to a solid support by standard means.

"reproductive unit or structure" of a plant is any totipotent part or tissue of the plant from which one can obtain a progeny of the plant, including, for example, seeds, cuttings, buds, bulbs, somatic embryos, etc.

The term "female reproductive structure" as used herein means those portions of a plant which compose the carpel, or gynoecium (an old established term used with regard to the gynoecium is "pistil"). The carpel of a flower of a plant includes but is not limited to a stigma, style, ovary, and cells or tissues which comprise the stigma, style and ovary.

As used herein, the term "antibody" is used in its broadest sense to include naturally occurring and non-naturally occurring polyclonal and monoclonal antibodies, as well as a polypeptide fragment of an antibody that retains a specific binding activity of at least about $1\times10^5$ l/M for a PtM3 gene product (SEQ ID NO:4) or a homolog thereof (SEQ ID NO:5), such as PtM4 gene product. One skilled in the art would recognize that an antibody fragment such as a Fab, F(ab')$_2$ or Fv fragment can retain specific binding activity for a PtM3 gene product or a homolog thereof, thus, is included within the definition of an antibody. A non-naturally occurring antibody, or fragment thereof, such as a chimeric antibody or humanized antibody also is included within the meaning of the term antibody. Such a non-naturally occurring antibody can be constructed using solid phase peptide synthesis, produced recombinantly or obtained, for example, by screening a combinatorial library consisting of variable heavy chains and variable light chains as described by Huse et al., Science 246:1275–1281 (1989), which is incorporated herein by reference.

An antibody "specific for" a polypeptide, or that "specifically binds" a polypeptide, binds with substantially higher affinity to that polypeptide than to an unrelated polypeptide. An antibody specific for a polypeptide also can have specificity for a related polypeptide. For example, an antibody specific for an Aspen PtM3 polypeptide or a homolog thereof, can specifically bind another plant PtM3 polypeptide or a homolog, such as an angiosperm, specifically, such as *Arabidopsis thaliana* PtM3 polypeptide or a tobacco PtM3 polypeptide. An antibody specific for an antigenic determinant or a epitopic region which consists of virtually any detectable epitope varying in amino acid length, that may be employed as a screenable marker, can be selected from the extremely wide variety of antigen:antibody combinations known to those of skill in the art. The unique extracellular epitope, whether derived from PtM3 or any other protein or epitopic substance, can then be straightforwardly detected using antibody labeling in conjunction with chromogenic or fluorescent adjuncts.

The invention encompasses the production of an antibody to the PtM3 protein, homologs and orthologs and functional fragments thereof. Monoclonal or polyclonal antibodies may be produced to either the normal PtM3 protein or mutated forms of this protein. The determination that an antibody specifically detects the PtM3 protein is made by any one of a number of standard immunoassay methods; for instance, the Western blotting technique (Sambrook et al., 1989). To determine that a given antibody preparation (such as one produced in a mouse) specifically detects the PtM3 protein by Western blotting, total cellular protein is extracted from rice cells and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect the PtM3 protein will, by this technique, be shown to bind to the PtM3 protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-PtM3 protein binding.

Substantially pure PtM3 protein suitable for use as an immunogen is isolated from rice cells or other cells in which it is produced, as described. Concentration of protein in the final preparation is adjusted, for example, by concentration on an Amicon filter device, to the level of a few micrograms per milliliter. Monoclonal or polyclonal antibody to the protein can then be prepared as follows:

Monoclonal antibody to epitopes of the PtM3 protein identified and isolated as described can be prepared from murine hybridomas according to the classical method of Kohler and Milstein (1975). *Nature* 256:495, or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980). *Enzymol.* 70:419, and derivative methods thereof. Selected positive clones can be expanded and their monoclonal antibody product harvested for use. Detailed procedures for monoclonal antibody production are described in Harlow and Lane (1988). *Antibodies, A Laboratory Manual*, Cold Spring Harbor Laboratory, New York.

Polyclonal antiserum containing antibodies to heterogenous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis et al. (1971). *J. Clin. Endocrinol. Metab.* 33:988–991.

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (1973). In *Handbook of Experimental Immunology*, Wier, D. (ed.) chapter 19. Blackwell. Plateau concentration of antibody is usually in the range of 0.1 to 0.2 mg/ml of serum. Affinity of the antisera for the antigen is determined by preparing competitive binding curves, as described, for example, by Fisher (1980). *Manual of Clinical Immunology*, Ch. 42.

A third approach to raising antibodies against the PtM3 protein is to use synthetic peptides synthesized on a commercially available peptide synthesizer based upon the predicted amino acid sequence of the PtM3 protein.

Antibodies may be raised against the PtM3 protein by subcutaneous injection of a DNA vector which expresses the PtM3 protein into laboratory animals, such as mice. Delivery of the recombinant vector into the animals may be achieved using a hand-held form of the Biolistic system as described by Tang et al. (1992). *Nature* (London) 356: 152–154.

Antibody preparations prepared according to these protocols are useful in quantitative immunoassays which determine concentrations of antigen-bearing substances in biological samples; they are also used semi-quantitatively or qualitatively to identify the presence of antigen in a biological sample.

The term "in situ hybridization" refers to a number of techniques have been developed in which nucleic-acid probes are used to locate specific DNA sequences on intact chromosomes in situ, a procedure called "in situ hybridization." See, e.g., Pinkel et al., *Proc. Natl. Acad. Sci.* USA 85:9138–9142, 1988 (regarding fluorescence in situ hybridization), and Lengauer et al., *Hum. Mol. Genet.* 2:505–512, 1993 (regarding "chromosomal bar codes"). Well-known methods for in situ hybridization and for the preparation of probes or primers for such methods are employed in the practice of the present invention, including direct and indirect in situ hybridization methods.

All publications cited herein are incorporated by reference to the same extent as if each individual publication was specifically and individually indicated to be incorporated by reference. The invention now being fully described, it will be apparent to one of ordinary skill in the art that many changes and modifications can be made thereto without departing from the spirit or scope of the claims.

The terms used in this specification generally have their ordinary meanings in the art, within the context of the invention, and in the specific context where each term is used. Certain terms are defined above, or elsewhere in the specification, to provide additional guidance to the person of skill in the art in describing the compositions and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

EXAMPLE 1

Use of the *Populus* cDNAs and Promoters to Modify Fertility Characteristics

Once a nucleic acid encoding a protein involved in the determination of a particular plant characteristic, such as flowering, has been isolated, standard techniques may be used to express the nucleic acid in transgenic plants in order to modify that particular plant characteristic. One approach is to clone the nucleic acid into a vector, such that it is operably linked to control sequences (e.g., a promoter) which direct expression of the nucleic acid in plant cells. The transformation vector is then introduced into plant cells by one of a number of techniques (e.g., *Agrobacterium*-mediated transformation) and progeny plants containing the introduced nucleic acid are selected. All or part of the transformation vector may stably integrate into the genome of the plant cell. That part of the vector which integrates into the plant cell and which contains the introduced nucleic acid and associated sequences for controlling expression (the introduced "transgene") may be referred to as the transgenic expression cassette.

Selection of progeny plants containing the introduced transgene may be made based upon the detection of an altered phenotype. Such a phenotype may result directly from the nucleic acid cloned into the transformation vector or may manifest as enhanced resistance to a chemical agent (such as an antibiotic) as a result of the inclusion of a dominant selectable marker gene incorporated into the transformation vector.

The choice of (a) control sequences and (b) how the nucleic acid (or selected portions of the nucleic acid) are arranged in the transformation vector relative to the control sequences determine, in part, how the plant characteristic affected by the introduced nucleic acid is modified. For example, the control sequences may be tissue specific, such that the nucleic acid is only expressed in particular tissues of the plant (e.g., reproductive tissues) and so the affected characteristic will be modified only in those tissues. The nucleic acid sequence may be arranged relative to the control sequence such that the nucleic acid transcript is expressed normally, or in an antisense orientation. Expression of an antisense RNA that is the reverse complement of the cloned nucleic acid will result in a reduction of the targeted gene product (the targeted gene product being the protein encoded by the plant gene from which the introduced nucleic acid was derived). Over-expression of the introduced nucleic acid, resulting from a plus-sense orientation of the nucleic acid relative to the control sequences in the vector, may lead to an increase in the level of the gene product, or may result in a reduction in the level of the gene product due to co-suppression (also termed "sense suppression") of that gene product. In another approach, the nucleic acid sequence may be modified such that certain domains of the encoded peptide are deleted. Depending on the domain deleted, such modified nucleic acid may act as dominant negative mutations, suppressing the phenotypic effects of the corresponding endogenous gene.

Successful examples of the modification of plant characteristics by transformation with cloned nucleic acid sequences are replete in the technical and scientific literature. Selected examples, which serve to illustrate the level of knowledge in this field of technology include:

U.S. Pat. No. 5,432,068 (control of male fertility using externally inducible promoter sequences);
U.S. Pat. No. 5,686,649 (suppression of plant gene expression using processing-defective RNA constructs);
U.S. Pat. No. 5,659,124 (transgenic male sterile plants);
U.S. Pat. No. 5,451,514 (modification of lignin synthesis using antisense RNA and co-suppression);
U.S. Pat. No. 5,443,974 (modification of saturated and unsaturated fatty acid levels using antisense RNA and co-suppression);
U.S. Pat. No. 5,530,192 (modification of amino acid and fatty acid composition using antisense RNA);
U.S. Pat. No. 5,455,167 (modification of medium chain fatty acids)
U.S. Pat. No. 5,231,020 (modification of flavonoids using co-suppression);
U.S. Pat. No. 5,583,021 (modification of virus resistance by expression of plus-sense RNA); and
Mizukami et al. (1996). Plant Cell 8:831–845 (dominant negative mutations in floral development using partial deletions of AG).

These examples include descriptions of transformation vector selection, transformation techniques and the production of constructs designed to over-express an introduced nucleic acid, dominant negative mutant forms, untranslatable RNA forms or antisense RNA. In light of the foregoing and the provision herein of the PtM3 and PtM4 cDNA and gene sequences, it is apparent that one of skill in the art may be able to introduce these cDNAs or genes, or derivative forms of these sequences (e.g., antisense forms), into plants in order to produce plants having modified fertility characteristics, particularly sterility. This Example provides a description of the approaches that may be used to achieve this goal. For convenience, the PtM3 and PtM4 cDNAs and genes disclosed herein will be generically referred to as the "floral reproductive genes," and the encoded polypeptides as the "floral reproductive gene products" or "floral reproductive polypeptide". Example 6 provides an exemplary illustration of how an antisense or inverted repeat form of one of these floral reproductive genes, specifically the PTD cDNA, may be introduced into angiosperms such as tobacco and *Arabidopsis* using *Agrobacterium* transformation, in order to produce genetically engineered sterile angiosperms. Example 5 provides an exemplary illustration of how increased expression of PtM3 cDNA may be produced and introduced into angiosperm species to produce modified fertility characteristics, such as early flowering, increased branching, increased flower pod production, and conversion of axillary meristems to floral meristems.

a. Vector Construction, Choice of Promoters

A number of recombinant vectors suitable for stable transfection of plant cells or for the establishment of transgenic plants have been described including those described in Pouwels et al. (1987). Cloning Vectors: A Laboratory Manual, 1985 supplement; and Weissbach and Weissbach (1989). Methods for Plant Molecular Biology, Academic Press. Typically, plant transformation vectors include one or more cloned plant genes (or cDNAs) under the transcriptional control of 5' and 3' regulatory sequences and a dominant selectable marker. Such plant transformation vectors typically also contain a promoter regulatory region (e.g., a regulatory region controlling inducible or constitutive, environmentally or developmentally regulated, or cell-, tissue-, or temporal-specific expression), a transcription initiation start site, a ribosome binding site, an RNA processing signal, a transcription termination site, and/or a polyadenylation signal.

Examples of plant promoters which may be useful for expressing the floral reproductive genes are provided herein above.

The promoter regions of the PtM3 or PtM4 gene sequences confer floral-specific (or floral-enriched) expression in *Populus*. Accordingly, these native promoters may be used to obtain floral-specific (or floral-enriched) expression of the introduced transgene.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Also, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

b. Arrangement of Floral Reproductive Gene Sequence in Vector

Modified fertility characteristics in plants may be obtained using the floral reproductive gene sequences disclosed herein in a variety of forms. Over-expression, sense-suppression, antisense RNA, inverted repeats and dominant negative mutant forms of the disclosed floral reproductive gene sequences may be constructed in order to modulate or supplement the expression of the corresponding endogenous floral reproductive genes, and thereby to produce plants having modified fertility characteristics. Alternatively, the floral-specific (or floral-enriched) expression conferred by the promoters of the disclosed floral reproductive genes may be employed to obtain corresponding expression of cytotoxic products. Such constructs will comprise the appropriate floral reproductive promoter sequence operably linked to a suitable open reading frame (discussed further below) and will be useful in genetic ablation approaches to engineering sterility in plants.

i. Modulation/Supplementation of Floral Reproductive Gene Expression

The particular arrangement of the floral reproductive gene sequence in the transformation vector will be selected according to the type of expression of the sequence that is desired.

Enhanced expression of a floral reproductive gene may be achieved by operably linking the floral reproductive gene to a constitutive high-level promoter such as the CaMV 35S promoter. As noted below, modified activity of a floral reproductive gene product in plants may also be achieved by introducing into a plant a transformation vector containing a variant form of a floral reproductive gene, for example a form which varies from the exact nucleotide sequence of the disclosed floral reproductive gene.

A reduction in the activity of a floral reproductive polypeptide in the transgenic plant may be obtained by introducing into plants antisense constructs based on the floral reproductive gene sequence. For expression of antisense RNA, the floral reproductive gene is arranged in reverse orientation relative to the promoter sequence in the transformation vector. The introduced sequence need not be the full-length floral reproductive gene, and need not be exactly homologous to the floral reproductive gene found in the plant type to be transformed. Generally, however, where the introduced sequence is of shorter length, a higher degree of homology to the native floral reproductive gene sequence will be needed for effective antisense suppression. Suitably, the introduced antisense sequence in the vector will be at least 50 nucleotides in length, and improved antisense suppression will typically be observed as the length of the antisense sequence increases. Suitably, the length of the antisense sequence in the vector will be greater than 100 nucleotides. Transcription of an antisense construct as described results in the production of RNA molecules that are the reverse complement of mRNA molecules transcribed from the endogenous floral reproductive gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous floral reproductive polypeptide activity can also be achieved using ribozymes. Ribozymes are synthetic RNA molecules that possess highly specific endoribonuclease activity. The production and use of ribozymes are disclosed in U.S. Pat. No. 4,987,071 and U.S. Pat. No. 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Constructs in which the floral reproductive gene (or variants thereof) are over-expressed may also be used to obtain co-suppression of the endogenous floral reproductive gene in the manner described in U.S. Pat. No. 5,231,021. Such co-suppression (also termed sense suppression) does not require that the entire floral reproductive cDNA or gene be introduced into the plant cells, nor does it require that the introduced sequence be exactly identical to the endogenous floral reproductive gene. However, as with antisense suppression, the suppressive efficiency will be enhanced as (1) the introduced sequence is lengthened and (2) the sequence similarity between the introduced sequence and the endogenous floral reproductive gene is increased.

Constructs expressing an untranslatable form of the floral reproductive gene mRNA may also be used to suppress the expression of endogenous floral reproductive genes. Methods for producing such constructs are described in U.S. Pat. No. 5,583,021. Such constructs are made by introducing a premature stop codon into the floral reproductive ORF.

Finally, dominant negative mutant forms of the disclosed sequences may be used to block endogenous floral reproductive polypeptide activity using approaches similar to that described by Mizukami et al. (1996). *Plant Cell* 8:831–845.

Such mutants require the production of mutated forms of the floral reproductive polypeptide that bind either to an endogenous binding target (for example, a nucleic acid sequence in the case of floral reproductive polypeptides, such as PtM3 and PtM4, that function as transcription factors) or to a second polypeptide sequence (such as transcription co-factors), but do not function normally after such binding (i.e. do not function in the same manner as the non-mutated form of the polypeptide). By way of example, such dominant mutants can be constructed by deleting all or part of the C-terminal domain of a floral reproductive polypeptide, leaving an intact MADS domain. Polypeptides lacking all or part of the C-terminal region may bind to the appropriate DNA target, but are unable to interact with protein co-factors, thereby blocking transcription. Alternatively, dominant negative mutants may be produced by deleting all or part of the MADS domain, or all or part of the K-domain.

ii. Genetic Ablation

An alternative approach to modulating floral development is to specifically target a cytotoxic gene product to the floral tissues. This may be achieved by producing transgenic plants that express a cytotoxic gene product under the control of a tissue- and temporal-specific promoter, such as the promoter region of PtM3 as disclosed herein. The promoter region of this gene sequence is generally contained within the first 150 base pairs of sequence upstream of the open reading frame, although tissue- and temporal-specific expression may be conferred by using smaller regions of this sequence. Thus, regions as small as the first 50 base pairs of sequence upstream of the open reading frame may be effective in conferring tissue- and temporal-specific expression. However, longer regions, such as at least 100, 150, 200 or 250 base pairs of the upstream sequences are preferred.

A number of known cytotoxic gene products may be expressed under the control of the disclosed promoter sequences of the floral reproductive gene. These include: RNases, such as barnase from *Bacillus* amyloliquefaciens and RNase-T1 from *Aspergillus*; Mariani et al. (1992). A chimeric ribonuclease-inhibitor gene restores fertility to male-sterile plants. *Nature* 357:384–387; ADP-ribosyltransferase (Diphtheria toxin A chain); Kandasamy et al. (1993). Ablation of papillar cell finction in *Brassica* flowers results in the loss of stigma receptivity to pollination. *Plant Cell* 5:263–275; RolC from *Agrobacterium* rhizogenes; Schmulling et al. (1993). Resoration of fertility by antisense RNA in genetically engineered male sterile tobacco plants. *Mol. Gen. Genet.* 237-385–394; DTA (diphtheria toxin A); Pappenheimer (1977). Diphtheria toxin. *Annu. Rev. Biochem.* 46:69–94; and glucanase (Worrall et al. (1992). Premature dissolution of the microporocyte callose wall causes male sterility in transgenic tobacco. *Plant Cell* 4:759–771).

c. Transformation and Regeneration Techniques

Constructs designed as discussed above to modulate or supplement expression of native floral reproductive genes in plants, or to express cytotoxins in a tissue- and temporal-specific manner can be introduced into plants by a variety of means. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited electroporation of plant protoplasts; liposome-mediated transformation; polyethylene mediated transformation; transformation using viruses; micro-injection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

Methods that are particularly suited to the transformation of woody species include (for *Picea* species) methods described in Ellis et al. (1993). *Bio/Technology* 11:84–89; and (for *Populus* species) the use of *A.* tumefaciens (Stettler (1993). *Popular Molecular Network Newsletter* 1(1), College of Forest Resources AR-10, University of Washington, Seattle, Wash.; Strauss et al. (1995a). *Molecular Breeding* 1:5–26; Strauss et al. (1995b). *TGERC Annual Report: 1994–1995*. Forest Research Laboratory, Oregon State University), *A.* rhizogenes (Han et al. (1996). Cellular and molecular biology of *Agrobacterium*-mediated transformation of plants and its application to genetic transfonnation of *Populus*. In: Stettler et al. [eds.] Biology of *Populus* and its Implications for Management and Conservation, Part I, Chapter 9, pp. 201–222, NRC Research Press, Nat. Res. Coun. of Canada, Ottawa, Ontario) and biolistics (McCown et al. (1991), stable transformation of *Populus* and incorporation of pest resistance by electric discharge particle acceleration. *Plant Cell Rep.* 9:590–594).

d. Selection of Transformed Plants

Following transformation and regeneration of plants with the transformation vector, transformed plants are suitably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, the effect on fertility can be determined by visual inspection of floral morphology, including the determination of the production of pollen or ova. In addition, the effect on the activity of the endogenous floral reproductive gene may be directly determined by nucleic acid analysis (hybridization or PCR methodologies) or immunoassay (western blot) of the expressed protein. Antisense or sense suppression of the endogenous floral reproductive gene may be detected by analyzing mRNA expression on Northern blots or by reverse transcription polymerase chain reaction (RT-PCR).

EXAMPLE 2

Cloning and Sequence Analysis of PtM3 and PtM4 cDNA

MADS-box cDNA homologs were cloned from male (PtM3) and female (PtM4) aspen (*Populus tremuloides*). PtM3 and PtM4 clones were first isolated by Reverse transcription-Polymerase chain reaction (RT-PCR) using RNA extracted from *Populus* cells as a template. The gene sequences may also be directly amplified using *Populus* genomic DNA as a template. Methods and conditions for both direct PCR and RT-PCR are known in the art and are described in Innis et al. (1990). *PCR Protocols, A Guide to Methods and Applications*, Innis et al. [eds.], Academic Press, Inc., San Diego, Calif. The RT-PCR procedure was followed by screening a cDNA library from developing male and female aspen flowers (Ausubel et al., 1989. *Current Protocols*, Wiley Publishers, NY). Suitable plant cDNA and genomic libraries for direct PCR include *Populus* libraries made by methods described therein. Other tree cDNA and genomic libraries may also be screened in order to, amplify orthologous cDNAs of tree species, such as *Pinus* and *Eucalyptus*.

The full-length nucleotide sequences of PTM3 and PTM4 was obtained by using similar PCR primer sets. One set of external PCR primers was used to obtain the PCR product and two sets of nested internal PCR primers were used to confirm the PCR products obtained from the external primers. The oligonucleotide sequences of the external primers are as follows: 5' primer (cDNA5'S1)-5' GTTAAG-GAATATGGGGAGAGGTAGAGTGG 3' (SEQ ID NO:6) and 3' primer (cDNA3'ASb)-5' GTCCCTGGCTAAAGT-TCTGAAATCCAGCCAC 3' (SEQ ID NO:7). The 5' internal set of primers used to confirm the PCR products obtained from the external primers are as follows: 5' internal primer 1 (cDNA5'S2)-5' GATAGAGAACAAGATAAACAG-GCAGGTGA 3' (SEQ ID NO:8) and 3' internal primer 2 (FAGL4-AS1)-5' GTTCCTCTGAGTTCGTTGTAGGGC 3' (SEQ ID NO:9). The 3' internal set of primers used to confirm the PCR products obtained from the external primers are as follows: 5' internal primer 1 (FAGL4-S1)-5' CAAGATTTGAGGCCCTACAACGA 3' (SEQ ID NO:10) and 3' internal primer 2 (cDNA3'ASb)-5' GTCCCTG-GCTAAAGTTCTGAAATCCAGCCAC 3' (SEQ ID NO:11). These primers are illustrative only; it will be appreciated by one skilled in the art that many different primers may be derived from a cDNA or a full-length gene sequence in order to amplify particular regions. Suitable amplification conditions for PtM3 and PtM4 include those described herein (See, e.g., Innis et al. (1990)). As is well known in the art, amplification conditions may nee d to be varied in order to amplify orthologous genes where the sequence identity is not 100%; in such cases, the use of nested primers, as described in (Ausbel 1989) may be beneficial. Resequencing of PCR products obtained by these amplification procedures is recommended; this will facilitate confirmation of the amplified cDNA sequence and will also provide information on natural variation on this sequence in different ecotypes, cultivars and plant populations.

Oligonucleotides that are derived from the PtM3 or PtM4 cDNA and gene sequences and which are suitable for use as PCR primers to amplify corresponding nucleic acid sequences are encompassed within the scope of the present invention. Such oligonucleotide primers will comprise a sequence of 15–20 consecutive nucleotides of the selected cDNA or gene sequence. To enhance amplification specificity, primers comprising at least 25, 30, 35, 50 or 100 consecutive nucleotides of the PtM3 or PtM4 gene or cDNA sequences may be used.

The nucleotide sequences of PtM3 and PtM4 cDNAs and the PtM3 5' untranslated region containing the promoter (See Example 3) were determined using the dideoxy chain termination method (Sanger et al., 1977. *Proc. Natl. Acad. Sci.* 74: 5463–5467). FIG. 1 illustrates the polynucleotide (SEQ ID NO:1) sequence and the corresponding amino acid (SEQ ID NO:4) sequence of Aspen PtM3. FIG. 2 shows the polynucleotide (SEQ ID NO:2) sequence and the corresponding amino acid (SEQ ID NO:5) sequence of Aspen PtM4. FIG. 3 shows the predicted amino acid sequence alignment between Aspen PtM3 and Aspen PtM4, wherein the sequence identity between the two homologs is found to be 97% using the Clustal W sequence alignment algorithm.

Figure 4:
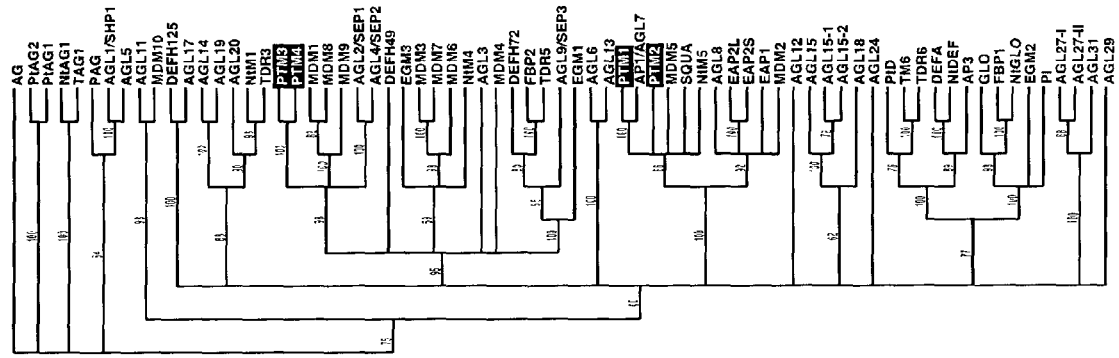
FIG. 4 illustrates the phylogenetic tree of predicted amino acid sequences of PtM1, PtM2, PtM3 (male dominant expression) and PtM4 (female dominant expression) compared to various floral and tree MADS-box sequences. The phylogenetic tree including several MADS-box genes is shown in FIG. 4, indicating that PtM3 and PtM4 occupy a separate branch and are not identical to *Arabidopsis* AGL (Sepallata) genes. The phylogenetic analysis was obtained by heuristic search algorithms using the PAUP (Phylogenetic Analysis Using Parsimony) version 4.0 beta 4a software tool for comparative biological sequence analysis. Starting with a set of aligned sequences, a search was performed for phylogenetic trees that were optimal (standard default parameters may be applied). Heuristic search analysis was done on sequence alignments followed by Bootstrap analysis using 100 replicates. Branch numbers refer to the number of replicates that support the branch. Accession numbers of sequences and names of plant species are provided immediately below.

Based on sequence level similarity, it was determined that PtM3 and PtM4 belong to the SEP1/2 family of genes, which includes AGL2/SEP1, AGL4/SEP2 from *Arabidopsis*, and DEFH49 from *Antirrhinum* (Pelaz et al., 2000; Angenent et al, 1992; Davies et al., 1996) (FIG. 4). However, at the amino acid level, it appears that PtM3/PtM4 share 76% identity with AGL2/SEP1, 75% with AGL4/SEP2, and 68% with DEFH49. Regardless, it should be noted that this is the first instance where PtM3 and PtM4 have been identified to have the same MADS-box family gene from the male and female flowers of a dioecious tree species. Both, PtM3 and PtM4 were found to be expressed during early stages of flower development in aspen and thus have potential to control flowering in aspen and other related tree species. Furthermore, while the PtM3 and PtM4 sequences show some similarity to *Arabidopsis* Sepellata genes (See, Pelaz et al) the % sequence identity is not enough to classify them as Sepallata group genes.

EXAMPLE 3

PtM3 Promoter Isolation and Sequence Analysis

The promoter region for PtM3 was also cloned. The promoter region of PtM3 was isolated using the Genome Walker kit purchased from Clontech (Clontech, Calif.). The promoter region of PtM3 contained the motifs characteristic of MADS-box gene promoters such as CArG boxes as determined by searching with the Genomatix software at http://www.genomatix.de/mat_fam. (See, GenomatixUSA, 1776 Mentor Avenue, Cincinnati, Ohio, 45212, USA; Toll-Free: (888) 236-3029)

FIG. 5 sets forth the 5'-untranslated region (UTR) which includes the polynucleotide sequence of the PtM3 promoter along with the intron sequence. The PtM3 promoter contains a MADS-box sequence motif from nucleotides 1153 to 1441, which is believed to regulate gene expression by binding to sites, known as CArG boxes, TATA sequences, etc., present in the promoter regions of plant MADS-box genes (Riechmann et al., *Biol. Chem.* 378:1079–1101 (1998). The PtM3 promoter region sequence may be very useful in determining how PtM3 related genes are regulated in trees and how their expression is modulated during dormancy. Promoters from PtM3 or PtM4 may also be useful in developing sterile trees through selective inhibition of plant reproductive meristems. Since, expression of PtM3 and PtM4 may be controlled by a tissue and temporal specific promoter, constructing DNA constructs or expression cassettes with the PtM3 promoter may allow for repro-ductive tissue targeting and alteration of the timing of gene expression of desired genes and gene products as described below in Examples 4–6.

EXAMPLE 4

Developmental Regulation and Expression of PtM3

Expression of the antisense transgene was assessed in immature plants by extraction of mRNA and Northern blotting using the PTD cDNA as a probe, or by RT-PCR. Flower specific mRNA expression patterns of PtM3 and PtM4 were determined by using sequence specific primers followed by RT-PCR of mRNA from various developmental stages of aspen male and female flowers. RT-PCR products were then blotted and probed with specific DNA probes for PtM3 and PtM4. These experiments illustrated that both PtM3 and PtM4 were expressed from early stages of development and the expression of these genes varied in sexes.

In order to obtain the Northern blot shown in FIG. 6, total RNA (10 μg) from each developmental stage of female aspen flowers was fractionated on a 1.2% formaldehyde agarose gel and transferred to Hybond™ N-nylon membranes (purchased from Amersham). The Northern blot membrane was hybridized to $^{32}$P-labeled probe at 68° C. and washed at high stringency. The specific 3'UTR of PtM3 was used as probe. Panel A shows expression of PtM3 mRNA at specific flower bud developmental stages, as compared to control tissues (leaf and xylem RNA). Panel B shows expression of PtM4 mRNA at specific flower bud developmental stages, as compared to control tissues (leaf and xylem RNA). Panel C shows the differential expression of male PtM3 (M) and female (F) PtM4 floral buds from stage 4 as compared to leaf (L) and xylem (X) RNA. Panel D shows the result of having the 3'-UTR probe of PtM3 used to hybridize against total RNA from Stage 4 male and female buds. Based on expression patterns of PtM3 and PtM4, it appears that these genes are involved in the early stages of flower development. PtM3 and PtM4 have great potential to alter reproductive capacity of trees both to increase flowering time, and flower numbers and also to develop sterility. Also, levels of PtM3 and PtM4 protein were analyzed by extraction, purification and concentration of cellular proteins to perform in situ hybridization or to make antibodies for performing western or blots.

EXAMPLE 5

Phenotypic Alterations in Plants Resulting from Over-Expression of PtM3

The altered phenotypes of the transgenic plants over-expressing PtM3 were analyzed in the panels A–E of FIG. 7. Panel A, shows tobacco from transgenic line PtM3-21 (right) showing early flowering as compared to WT tobacco (left). This early flowering is a potentially useful trait for increased yield by allowing an increase in the number of crops per growing season. Additionally, early flowering could provide for the production of crops in conditions which would not normally generate satisfactory yield to a short growing season. Panel B, shows a T1 generation plant from one control construct line pTCS5. Panel C, shows a T1 generation plant from transgenic line PtM3-9-9. Panel D, shows a T3 generation transgenic *Arabidopsis* from line PtM3-4-3 (right) displaying increased branching and flower pod production as compared to WT (left). Panel E, shows a graph depicting the average seed yields (mg) and pod numbers in the transgenic PtM3-4-3 plants (right) as compared to WT (left).

The present invention is applicable to many hardwood tree species to control flowering including, Populus species, cottonwoods, Sweetgum, eucalyptus, fruit trees such as apple, peach, nut trees such as walnuts, pecans and almonds. Since ectopic over expression of PtM3 in herbaceous plants such as Arabidopsis and tobacco caused reduced juvenile periods resulting in accelerated and earlier flowering and increased fruit production (FIG. 7), it is likely that PtM3 and PtM4 can be used for crop plants also to increase seed output. Earlier flowering will allow for more rapid selective breeding programs for economically important trees. Increased branching and flower production will be useful for increasing yields of fruit and nut trees and increase flower yields for ornamentals. Further experiments have been conducted where the gene constructs containing Aspen PtM3 have been introduced into Aspen trees to develop overexpression in transgenic aspen where the juvenile period is reduced and flowering is accelerated.

EXAMPLE 6

Phenotypic Alterations in Plants Resulting from Suppressed Expression of PtM3

FIG. 8, Panels A–H illustrates the altered phenotypes of the transgenic plants with suppressed PtM3 expression. Panels A and B show a control plant and a plant with an antisense PtM3 incorporated into a plant, respectively. In panel A the control is flowering. In panel B, the antisense PtM3 tobacco plant is not flowering. In fact the antisense PtM3 containing plants mature, begin senescing and eventually die without flowering. Panel C shows a transgenic tobacco plant containing inverted repeats of a portion of the PtM3 sequence which does not form flowers, in comparison to the control plants that form normal flowers (panel D). Panels E and F show the absence of petals and stamens when an inverted repeat of male PtM3 is introduced into the bisexual tobacco plant. Only female sex organ is formed and can be pollinated by pollen from a control to form pods. These results show that the PtM3 may also have a role in the male sex determination. Panel G shows flowerless Arabidopsis terminal and Panel H shows normal pod development in control.

Antisense or inverted repeat constructs of PtM3 were used to suppress gene expression resulting in complete sterility or sterility of one of the sex organs in tobacco and Arabidopsis. Generating sterile trees for commercial fiber farming of trees with value added genes to meet the regulations by USDA, EPA, etc. Selective inhibition of either female or male organs will have significant use in breeding programs for various tree and perennial species. Also, reduced promoter activity from PtM3 will be useful in developing sterile trees by selective inhibition of reproductive meristems. Also, the inhibition of flowering using a PtM3-RNAse cassette or any other cytotoxic gene, may have an added benefit by preventing reproductive development at the earliest stage. The methods of the present invention result in an advantageous energy savings which allows the plant to increase the biomass through increased branching because the growing conditions are not limiting.

Since aspen is a dioecious tree (sexes are on different trees), PtM3 and PtM4 could also be used to control either male or female reproductive structures and will be useful for breeding. For example, transgenic aspen can be generated either to completely abolish flowering (sterility) or to reduce juvenile periods and to accelerate flowering so that these aspen plants can be used for breeding purposes within 2 years instead of the normal 6 to 8 years time period. Sterility through either using the PtM3 gene promoter controlling a cytotoxic RNAse gene or through using constructs with antisense or inverted repeat sequences of PtM3 cDNA may be very valuable for commercialization of genetically modified trees. Once the trees are sterilized additional genes with other useful traits in the forest products industry such as wood quality, rapid growth or pest and herbicide resistance can be introduced into the sterile tree. Also, since, trees like aspen can be vegetatively propagated, once a transgenic line with chosen phenotype is obtained it can be scaled up. The methods for generating transgenic aspen are available and are developed in our lab (Boerjan et al., 1997; Karnosky et al., 2000; Kim, J. H. 1998; Tsai et al, 1994; 1998).

EXAMPLE 7

Other Applications Using the Disclosed Sequences

The disclosed floral reproductive genes and polypeptides may be useful as laboratory reagents to study and analyze floral gene expression in plants, including plants engineered for modified fertility characteristics. For example, probes and primers derived from the PtM3 sequence, as well as monoclonal antibodies specific for the PtM3 polypeptide may be used to detect and quantify expression of PtM3 in seedlings transformed with an antisense PtM3 construct as described above. Such analyses would facilitate detection of those transformants that display modified PtM3 expression and which may therefore be good candidates for having modified fertility characteristics.

The production of probes and primers derived from the disclosed sequences is described in detail above. Production of monoclonal antibodies requires that all or part of the protein against which the antibodies to be raised be purified. With the provision herein of the floral reproductive gene sequences, as well as the sequences of the encoded polypeptides, this may be achieved by expression in heterologous expression systems, or chemical synthesis of peptide fragments.

Many different expression systems are available for expressing cloned nucleic acid molecules. Examples of prokaryotic and eukaryotic expression systems that are routinely used in laboratories are described in Sambrook et al. supra at Ch. 16–17. Such systems maybe used to express the floral reproductive polypeptides at high levels to facilitate purification.

By way of example only, high level expression of a floral reproductive polypeptide may be achieved by cloning and expressing the selected cDNA in yeast cells using the pYES2 yeast expression vector (Invitrogen, San Diego, Calif.). Secretion of the recombinant floral homeotic polypeptide from the yeast cells may be achieved by placing a yeast signal sequence adjacent to the floral reproductive gene coding region. A number of yeast signal sequences have been characterized, including the signal sequence for yeast invertase. This sequence has been successfully used to direct the secretion of heterologous proteins from yeast cells, including such proteins as human interferon (Chang et al. (1986). *Saccharomyces cerevisiae* secretes and correctly processes human interferon hybrid protein containing yeast invertase signal peptides. *Mol. and Cell. Biol.* 6:1812–1819.) and human lactoferrin (Liang and Richardson (1993). Expression and characterization of human lactoferrin in yeast (*Saccharomyces cerevisiae*). *J. Agric. Food Chem.* 41:1800–1807). Alternatively, the enzyme may be expressed at high level in prokaryotic expression systems, such as in *E. coli.*

Monoclonal or polyclonal antibodies may be produced to the selected floral reproductive polypeptide, functionally equivalent fragments thereof or portions thereof. Optimally, antibodies raised against a specified floral reproductive polypeptide will specifically detect that polypeptide. That is, for example, antibodies raised against the PtM3 polypeptide would recognize and bind the PtM3 polypeptide and would not substantially recognize or bind to other proteins found in poplar cells. The determination that an antibody specifically detects PtM3 is made by any one of a number of standard immunoassay methods; for instance, the Western blotting technique (Sambrook et al., 1989). To determine that a given antibody preparation (such as one produced in a mouse against PtM3) specifically detects PtM3 by Western blotting, total cellular protein is extracted from poplar cells and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically detect PtM3 will, by this technique, be shown to bind to substantially only the PTD band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-PtM3 binding.

Substantially pure floral reproductive polypeptides suitable for use as an immunogen may be isolated from transformed cells as described above. Concentration of protein in the final preparation is adjusted, for example, by concentration on an Amicon filter device, to the level of a few micrograms per milliliter. Alternatively, peptide fragments of the specified floral reproductive polypeptide may be utilized as immunogens. Such fragments may be chemically synthesized using standard methods, or may be obtained by cleavage of the whole floral reproductive polypeptide followed by purification of the desired peptide fragments.

Peptides as short as 3 or 4 amino acids in length may be immunogenic when presented to the immune system in the context of a Major Histocompatibility Complex (MHC) molecule, such as MHC class I or MHC class II. Accordingly, peptides comprising at least 3 and suitably at least 4, 5, 6 or 10 or more consecutive amino acids of the disclosed floral reproductive polypeptide amino acid sequences may be employed as immunogens to raise antibodies. Because naturally occurring epitopes on proteins are frequently comprised of amino acid residues that are not adjacently arranged in the peptide when the peptide sequence is viewed as a linear molecule, it may be advantageous to utilize longer peptide fragments from the floral reproductive polypeptide amino acid sequences in order to raise antibodies. Thus, for example, peptides that comprise at least 10, 15, 20, 25 or 30 consecutive amino acid residues of the floral reproductive polypeptide amino acid sequence may be employed. Monoclonal or polyclonal antibodies to the intact floral reproductive polypeptide or peptide fragments of this protein may be prepared as described below.

Monoclonal antibody to epitopes of the selected floral reproductive polypeptide can be prepared from murine hybridomas according to the classical method of Kohler and Milstein (1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones may be identified by detection of antibody in the supernatant fluid of the wells by immunoassay procedures, such as ELISA, as originally described by Engvall (1980); and derivative methods thereof. Selected positive clones can be expanded and their monoclonal antibody product harvested for use. Detailed procedures for monoclonal antibody production are described in Harlow and Lane (1988). *Antibodies: A Laboratory Manual*, Cold Spring Harbor Laboratory, New York.

Having illustrated and described the principles of isolating the full-length floral reproductive genes, methods and kits for expressing the proteins encoded by these genes to obtain a variety of desired phenotypes, it should be apparent to one skilled in the art that the invention can be modified in arrangement and detail without departing from such principles. We claim all modifications coming within the spirit and scope of the claims presented herein.

What is claimed is:

1. An isolated polynucleotide encoding a polypeptide, wherein the polypeptide comprises SEQ ID NO:4.

2. An isolated polynucleotide comprising the coding sequence of SEQ ID NO:1, the complement of the coding sequence of SEQ ID NO:1, the reverse complement of the coding sequence of SEQ ID. NO:1, the full-length reverse sequence of the coding sequence of SEQ ID. NO:1, or a combination thereof.

3. An isolated polynucleotide comprising:
   (a) SEQ ID NO:1
   (b) the full-length complement of SEQ ID NO:1

(c) the reverse full-length complement of SEQ ID NO:1 or (d) the reverse full-length sequence of SEQ ID NO:1.

4. An isolated polynucleotide encoding a polypeptide having at least 97% amino acid sequence identity to SEQ ID NO:4.

5. A construct comprising:
a polynucleotide encoding a polypeptide, wherein the polypeptide comprises an amino acid sequence having at least 97% identity to SEQ ID NO:4, said polynucleotide operably linked to a promoter.

6. An isolated host cell transformed with the construct as set forth in claim 5.

7. A transgenic plant comprising at least one construct of claim 5.

8. A transgenic tree comprising at least one construct of claim 5.

9. A construct as set forth in claim 5, wherein the construct further comprises a promoter selected from the group consisting of a constitutive promoter, a tissue-specific promoter, a temporal-specific promoter, a developmentally regulated promoter, and a combination thereof.

10. A method of altering a characteristic of a plant, comprising transforming the plant with the construct as set forth in claim 5, wherein the altered characteristic is selected from the group consisting of accelerated flowering time, increased flowering number, increased fruit production, increased nut production, increased seed output, increased branching, conversion of axillary meristems to floral meristems, increased reproductive capacity of sex organs, early reproductive development, and combinations thereof compared to a control plant that is not transfonned with the construct.

11. The method as set forth in claim 10, wherein the plant exhibits increased biomass.

12. A method of producing a transgenic plant having at least one altered characteristic compared to a nontransgenic control plant, wherein the method comprises:
(a) introducing into a plant cell a polynucleotide encoding a polypeptide comprising SEQ ID NO:4, to yield a transformed cell; and
(b) generating the transgenic plant from the transformed cell, the plant having at least one altered characteristic selected from the group consisting of (i) axillary meristem converted to floral meristem; (ii) accelerated flowering; (iii) early reproductive development; (iv) increased fruit production; (v) earlier flowering times; (vi) increased seed output; (vii) increased branching; (viii) increased flower production; (ix) increased fruit yield; and (x) increased flower yields.

13. The method as set forth in claim 12, wherein the plant is selected from the group consisting of a herbaceous plant, a crop plant, a perennial plant, a hybrid plant, a seed plant, a flowering plant, a tobacco plant, and an *Arabidopsis* plant.

14. The method as set forth in claim 12, wherein the plant is a tree.

15. The method as set forth in claim 14, wherein the tree includes at least one of a dioecious tree, a hybrid tree, a bisexual tree, a hardwood tree, or a *Populus* tree.

16. The method as set forth in claim 14, wherein the tree is Aspen.

17. The method of altering the reproductive capacity of a plant comprising:
(a) stably transforming a plant cell with the construct of claim 5, wherein the polynucleotide is incorporated in the genome of the plant cell; and
(b) growing the plant cell to produce a regenerated plant capable of expressing a polypeptide encoded by the polynucleotide for a time sufficient to alter the reproductive capacity of the plant.

18. The method as set forth in claim 17, wherein the polypeptide is over-expressed.

19. A method of ectopically expressing a polypeptide encoded by a floral reproductive gene in a plant, comprising introducing into the genome of the plant the construct of claim 5.

20. A method of producing a transgenic plant having altered reproductive capacity compared to a nontransgenic control plant, the method comprising:
(a) introducing into a plant cell a polynucleotide encoding a polypeptide comprising SEQ ID NO:4 to yield a transformed cell;
(b) generating a transgenic plant from the transformed cell, wherein the plant has altered reproductive capacity.

21. The method as set forth in claim 20, wherein the plant is selected from the group consisting of a herbaceous plant, a crop plant, a perennial plant, a hybrid plant, a seed plant, a flowering plant, a tobacco plant, and an *Arabidopsis* plant.

22. The method as set forth in claim 20, wherein the plant is a tree.

23. The method as set forth in claim 22, wherein the tree is selected from the group consisting of a dioecious tree, a hybrid tree, a bisexual tree, a hardwood tree, and a *Populus* tree.

24. The method as set forth in claim 22, wherein the tree is Aspen.

25. The method as set forth in claim 20, further comprising introducing an additional exogenous nucleotide sequence into the genome of the plant, wherein a polypeptide encoded by the additional exogenous nucleotide sequence is expressed in the plant, such that the plant exhibits increased herbicide resistance.

26. The method as set forth in claim 20, wherein the altered plant characteristic is selected front the group consisting of increased plant biomass, reduced pollen production and combinations thereof.

27. A plant produced by the method of claim 12.

28. A plant produced by the method of claim 17.

29. A plant produced by the method of claim 19.

30. A plant produced by the method of claim 20.

* * * * *